US007323549B2

(12) United States Patent
Lauder et al.

(10) Patent No.: US 7,323,549 B2
(45) Date of Patent: Jan. 29, 2008

(54) IL-7 FUSION PROTEINS

(75) Inventors: Scott Lauder, Boxborough, MA (US); Stephen D. Gillies, Carlisle, MA (US)

(73) Assignee: EMD Lexigen Research Center Corp., Billerica, MA (US)

( * ) Notice: Subject to any disclaimer, the term of this patent is extended or adjusted under 35 U.S.C. 154(b) by 0 days.

(21) Appl. No.: 11/027,446

(22) Filed: Dec. 30, 2004

(65) Prior Publication Data

US 2005/0164352 A1 Jul. 28, 2005

Related U.S. Application Data

(60) Provisional application No. 60/533,406, filed on Dec. 30, 2003.

(51) Int. Cl.
*C07K 14/54* (2006.01)
*C07K 16/00* (2006.01)
*C07K 1/00* (2006.01)

(52) U.S. Cl. .................... 530/387.1; 530/350; 530/351

(58) Field of Classification Search ..................... None
See application file for complete search history.

(56) References Cited

U.S. PATENT DOCUMENTS

| | | | | |
|---|---|---|---|---|
| 4,196,265 | A | 4/1980 | Koprowski et al. | |
| 4,469,797 | A | 9/1984 | Albarella | |
| 4,676,980 | A | 6/1987 | Segal et al. | |
| 5,019,368 | A | 5/1991 | Epstein et al. | |
| 5,082,658 | A | 1/1992 | Palladino | |
| 5,091,513 | A | 2/1992 | Huston et al. | |
| 5,114,711 | A | 5/1992 | Bell et al. | |
| 5,116,964 | A | 5/1992 | Capon et al. | |
| 5,194,596 | A * | 3/1993 | Tischer et al. | 530/399 |
| 5,196,320 | A | 3/1993 | Gillies | |
| 5,225,538 | A | 7/1993 | Capon et al. | |
| 5,258,498 | A | 11/1993 | Huston et al. | |
| 5,314,995 | A | 5/1994 | Fell, Jr. et al. | |
| 5,348,876 | A | 9/1994 | Michaelsen et al. | |
| 5,349,053 | A | 9/1994 | Landolfi | |
| 5,350,836 | A * | 9/1994 | Kopchick et al. | 530/399 |
| 5,359,035 | A | 10/1994 | Habermann | |
| 5,399,346 | A | 3/1995 | Anderson et al. | |
| 5,428,130 | A | 6/1995 | Capon et al. | |
| 5,480,981 | A | 1/1996 | Goodwin et al. | |
| 5,514,582 | A | 5/1996 | Capon et al. | |
| 5,541,087 | A | 7/1996 | Lo et al. | |
| 5,585,097 | A | 12/1996 | Bolt et al. | |
| 5,601,819 | A | 2/1997 | Wong et al. | |
| 5,609,846 | A | 3/1997 | Goldenberg | |
| 5,614,184 | A | 3/1997 | Sytkowski et al. | |
| 5,624,821 | A | 4/1997 | Winter et al. | |
| 5,645,835 | A | 7/1997 | Fell, Jr. et al. | |
| 5,650,150 | A | 7/1997 | Gillies | |
| 5,677,425 | A | 10/1997 | Bodmer et al. | |
| 5,679,543 | A | 10/1997 | Lawlis | |
| 5,709,859 | A | 1/1998 | Aruffo et al. | |
| 5,723,125 | A | 3/1998 | Chang et al. | |
| 5,726,044 | A | 3/1998 | Lo et al. | |
| 5,728,552 | A | 3/1998 | Fujisawa et al. | |
| 5,770,195 | A | 6/1998 | Hudziak et al. | |
| 5,827,516 | A | 10/1998 | Urban et al. | |
| 5,827,703 | A | 10/1998 | Debs et al. | |
| 5,843,423 | A | 12/1998 | Lyman et al. | |
| 5,908,626 | A | 6/1999 | Chang et al. | |
| 6,086,875 | A | 7/2000 | Blumberg et al. | |
| 6,100,387 | A | 8/2000 | Herrmann et al. | |
| 6,156,301 | A | 12/2000 | Namen et al. | |
| 6,169,070 | B1 | 1/2001 | Chen et al. | |
| 6,277,375 | B1 | 8/2001 | Ward | |
| 6,281,010 | B1 | 8/2001 | Gao et al. | |
| 6,284,536 | B1 | 9/2001 | Morrison et al. | |
| 6,309,636 | B1 | 10/2001 | de Couto et al. | |
| 6,335,176 | B1 | 1/2002 | Inglese et al. | |
| 6,410,008 | B1 | 6/2002 | Strom et al. | |
| 6,444,792 | B1 | 9/2002 | Gray et al. | |
| 6,475,717 | B1 | 11/2002 | Enssle et al. | |
| 6,485,726 | B1 | 11/2002 | Blumberg et al. | |
| 6,500,641 | B1 | 12/2002 | Chen et al. | |
| 6,551,592 | B2 | 4/2003 | Lindhofer et al. | |
| 6,617,135 | B1 | 9/2003 | Gillies et al. | |
| 6,620,413 | B1 | 9/2003 | DeSauvage et al. | |
| 6,627,615 | B1 | 9/2003 | Debs et al. | |
| 6,646,113 | B1 | 11/2003 | Dreyfuss et al. | |
| 6,750,329 | B1 | 6/2004 | Rosenblum et al. | |
| 6,838,260 | B2 | 1/2005 | Gillies et al. | |
| 6,969,517 | B2 | 11/2005 | Gillies et al. | |
| 6,992,174 | B2 | 1/2006 | Gillies et al. | |
| 7,067,110 | B1 | 6/2006 | Gillies et al. | |
| 7,091,321 | B2 | 8/2006 | Gillies et al. | |
| 7,141,651 | B2 | 11/2006 | Gillies et al. | |
| 7,148,321 | B2 | 12/2006 | Gillies et al. | |
| 7,169,904 | B2 | 1/2007 | Gillies et al. | |
| 7,186,804 | B2 | 3/2007 | Gillies et al. | |
| 2001/0053539 | A1 | 12/2001 | Lauffer et al. | |
| 2002/0034765 | A1 | 3/2002 | Daugherty et al. | |
| 2002/0037558 | A1 | 3/2002 | Lo et al. | |

(Continued)

FOREIGN PATENT DOCUMENTS

AU 21725/88 3/1989

(Continued)

OTHER PUBLICATIONS

Human IL-7, Uniprot accession No. P13232, release date Jan. 1, 1990.*

(Continued)

*Primary Examiner*—Gary B. Nickol
*Assistant Examiner*—Cherie Woodward
(74) *Attorney, Agent, or Firm*—Kirkpatrick & Lockhart Preston Gates Ellis LLP

(57) ABSTRACT

The invention is directed to a fusion protein which includes a first portion including an immunoglobulin (Ig) chain and a second portion including interleukin-7 (IL-7).

17 Claims, 16 Drawing Sheets

U.S. PATENT DOCUMENTS

| | | | |
|---|---|---|---|
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0133939 A1 | 7/2003 | Ledbetter et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166868 A1 | 9/2003 | Presta et al. |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |
| 2004/0180035 A1 | 9/2004 | Gillies et al. |
| 2004/0180386 A1 | 9/2004 | Carr et al. |
| 2004/0203100 A1 | 10/2004 | Gillies et al. |
| 2005/0042729 A1 | 2/2005 | Gillies et al. |
| 2005/0069521 A1 | 3/2005 | Gillies et al. |
| 2005/0137384 A1 | 6/2005 | Gillies et al. |
| 2005/0164352 A1 | 7/2005 | Lauder et al. |
| 2005/0192211 A1 | 9/2005 | Gillies et al. |
| 2005/0202021 A1 | 9/2005 | Gillies et al. |
| 2005/0202538 A1 | 9/2005 | Gillies et al. |
| 2005/0244418 A1 | 11/2005 | Gillies et al. |
| 2005/0260194 A1 | 11/2005 | Peters et al. |
| 2005/0261229 A1 | 11/2005 | Gillies et al. |
| 2006/0025573 A1 | 2/2006 | Gillies et al. |
| 2006/0034836 A1 | 2/2006 | Gillies et al. |
| 2006/0141581 A1 | 6/2006 | Gillies et al. |
| 2006/0194952 A1 | 8/2006 | Gillies et al. |
| 2006/0228332 A1 | 10/2006 | Gillies et al. |
| 2006/0263856 A1 | 11/2006 | Gillies et al. |
| 2007/0036752 A1 | 2/2007 | Gillies et al. |

FOREIGN PATENT DOCUMENTS

| | | |
|---|---|---|
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 601 043 B1 | 6/1994 |
| EP | 0 659 439 | 6/1995 |
| EP | 0 428 596 B1 | 4/1996 |
| EP | 0 706 799 A2 | 4/1996 |
| EP | 1 088 888 A1 | 4/2001 |
| EP | 1 176 195 | 1/2002 |
| WO | WO 86/01533 | 3/1986 |
| WO | WO 88/00052 | 1/1988 |
| WO | WO 88/07089 | 9/1988 |
| WO | WO 88/09344 | 12/1988 |
| WO | WO 89/02922 | 4/1989 |
| WO | WO 89/09620 | 10/1989 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 94/25609 | 11/1994 |
| WO | WO 95/05468 | 2/1995 |
| WO | WO 95/21258 | 8/1995 |
| WO | WO 95/31483 | 11/1995 |
| WO | WO 96/04388 | 2/1996 |
| WO | WO 96/08570 | 3/1996 |
| WO | WO 96/18412 | 6/1996 |
| WO | WO 96/40792 | 12/1996 |
| WO | WO 97/00317 | 1/1997 |
| WO | WO 97/00319 | 1/1997 |
| WO | WO 97/24137 | 7/1997 |
| WO | WO 97/24440 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/28427 | 7/1998 |
| WO | WO 98/30706 | 7/1998 |
| WO | WO 98/46257 | 10/1998 |
| WO | WO 98/52976 | 11/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 00/11033 | 3/2000 |
| WO | WO 00/34317 | 6/2000 |
| WO | WO 00/40615 | 7/2000 |
| WO | WO 00/47228 | 8/2000 |
| WO | WO 00/69913 | 11/2000 |
| WO | WO 01/07081 | 2/2001 |
| WO | WO 01/36489 | 5/2001 |
| WO | WO 01/58957 | 8/2001 |
| WO | WO 01/03737 | 1/2002 |
| WO | WO 02/02143 | 1/2002 |
| WO | WO 02/056910 | 7/2002 |
| WO | WO 02/066514 | 8/2002 |
| WO | WO 02/069232 | 9/2002 |
| WO | WO 02/072605 | 9/2002 |
| WO | WO 02/079232 | 10/2002 |
| WO | WO 02/090566 | 11/2002 |
| WO | WO 03/015697 | 2/2003 |
| WO | WO 03/048334 | 6/2003 |
| WO | WO 03/077834 | 9/2003 |
| WO | WO2004/018681 | 3/2004 |
| WO | WO2007/010401 | 1/2007 |

OTHER PUBLICATIONS

Mouse IL-7, UniProt accession No. P10168, release date Mar. 1, 1989.*
Parekh et al. TIBTECH, May 1989 7:117-122.*
Goochee et al., Biotechnology, Dec. 1991 9:1347-1355.*
Meier et al., Ther Immunol. Jun. 2, 1995(3):159-171, Abstract only.*
Benjamin et al., Development. 1998; 125:1591-1598.*
Vukicevic et al. PNAS USA. 1996; 93:9021-9026.*
Massague. Cell. 1987; 49:437-8.*
Pilbeam et al. Bone. 1993; 14:717-720.*
Skolnick et al. Trends in Biotech. 2000; 18:34-39.*
Bork. Genome Research. 2000; 10:398-400.*

Doerks et al. Trends in Genetics. 1998; 14:248-250.*
Smith et al. Nature Biotechnology. 1997; 15:1222-1223.*
Brenner. Trends in Genetics. 1999; 15:132-133.*
Bork et al. Trends in Genetics. 1996; 12:425-427.*
Bowie et al. Science. 1990; 247:1306-1310.*
Wells. Biochemistry. 1990; 29:8509-8517.*
Anderson et al., (1980), "Characterization of the Fc Receptor for IgG on a Human Macrophage Cell Line U937," *J. Immunol.*, 125(6):2735-41.
Angal et al., (1993), "A Single Amino Acid Substitution Abolishes the Heterogeneity of Chimeric Mouse/Human (IgG4) Antibody," *Molecular Immunology*, 30(1):105-108.
Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.
Batova et al., (1999), "The Ch14.18-GM-CSF Fusion Protein is Effective at Mediating Antibody-Dependent Cellular Cytotoxicity and Complement-Dependent Cytotoxicity in Vitro," *Clinical Cancer Research*, 5:4259-4263.
Batra et al., (1993), "Insertion of Constant Region Domains of Human IgG1 into CD4-PE40 Increases Its Plasma Half-Life," *Molecular Immunology*, 30(4):379-386.
Becker et al., (1996), "An Antibody-Interleukin 2 Fusion Protein Overcomes Tumor Heterogeneity by Induction of a Cellular Immune Response," *Proc. Natl. Acad. Sci. USA*, 93:7826-7831.
Becker et al., (1996), "Eradication of Human Hepatic and Pulmonary Medanoma Metastases in SCID Mice by Antibody-Interleukin 2 Fusion Proteins," *Proc. Natl. Acad. Sci. USA*, 93:2702-2707.
Becker et al., (1996), "Long-Lived and Transferable Tumor Immunity in Mice after Targeted Interleukin-2 Therapy," *J. Clin. Invest.*, 98(12):2801-2804.
Becker et al., (1996), "T Cell-Mediated Eradication of Murine Metastatic Melanoma Induced by Targeted Interleukin-2 Therapy," *J. Exp. Med.*, 183(50):2361-2366.
Beutler et al., (1988), "Tumor Necrosis, Cachexia, Shock, and Inflammation: A Common Mediator," *Annual Rev. Biochem.*, 57:505-518.
Bitonti et al. (2004), "Pulmonary Delivery of an Erythropoietin Fc Fusion Protein in Non-Human Primates Through an Immunoglobulin Transport Pathway," *Proc. Natl. Acad. Sci. USA*, 101(26):9763-9768.
Bitonti et al., (2002), "Transepithelial Absorption of an Erythropoietin-Fc Fusion Protein After Delivery to the Central Airways," *Respiratory Drug Delivery*, 8:309-312.
Bjorn et al., (1985), "Evaluation of Monoclonal Antibodies for the Development of Breast Cancer Immunotoxins," *Cancer Research*, 45:1214-1221.
Boulianne et al., (1984), "Production of Functional Chimaeric Mouse/Human Antibody," *Nature*, 312:643-6.
Bourgois et al., (1974), "Determination of the Primary Structure of a Mouse IgG2a Immunoglobulin: Amino- Acid Sequence of the Fc Fragment: Implications for the Evolution of Immunoglobulin Structure and Function," *Eur. J. Biochem.*, 43:423-35.
Brambell et al., (1964), "A Theoretical Model of γ-Globulin Catabolism," *Nature*, 203:1352-55.
Brekke et al., (1994), "Human IgG Isotype-Specific Amino Acid Residues Affecting Complement-Mediated Cell Lysis and Phagocytosis," *Eur. J. Immunol.*, 24:2542-2547.
Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.
Burgess et al., (1990), "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *Journal of Cell Biology*, 111:2129-2138.
Canfield et al., (1991), "The Binding Affinity of Human IgG for its High Affinity Fc Receptor is Determined by Multiple Amino Acids in the CH2 Domain and is Modulated by the Hinge Region," *J. Exp. Med.*, 173(6):1483-1491.
Capon et al., (1989), "Designing CD4 Immunoadhesins for AIDS Therapy," *Nature*, 337:525-531.
Caton et al., (1986), "Structural and Functional Implications of a Restricted Antibody Response to a Defined Antigenic Region on the Influenza Virus Hemagglutinin," *The EMBO Journal*, 5(7):1577-1587.
Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," *J. Immunol.*, 148:92-98.
Chapman et al., (1994), "Mapping Effector Functions of a Monoclonal Antibody to GD3 by Characterization of a Mouse-Human Chimeric Antibody," *Cancer Immuno. Immunother.*, 39:198-204.
Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.
Chaudhary et al., (1988), "Selective Killing of HIV-Infected Cells by Recombinant Human CD4-*Pseudomonas* Exotoxin Hybrid Protein," *Nature*, 335:370-372.
Chaudhary et al., (1989), "A Recombinant Immunotoxin Consisting of Two Antibody Variable Domains Fused to *Pseudomonas* Exotoxin," *Nature*, 339:394-397.
Cheon et al., (1994), "High-Affinity Binding Sites for Related Fibroblast Growth Factor Ligands Reside Within Different Receptor Immunoglobulin-Like Domains," *Proc. Natl. Acad. Sci. USA*, 91: 989-993.
Cohen et al., (1998), "An Artificial Cell-Cycle Inhibitor Isolated from a Combinatorial Library," *Proc. Natl. Acad. Sci. USA*, 95:14272-7.
Cole et al., (1997), "Human IgG2 Variants of Chimeric Anti-CD3 Are Nonmitogenic to T Cells," *Journal of Immunology*, 159:3613-3621.
Connor et al., (2004), "Ex vivo Evaluation of Anti-EpCAM Immunocytokine huKS-IL2 in Ovarian Cancer," *J. Immunotherapy*, 27:211-219.
Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.
Cruse et al., (eds.), (1995), *Illustrated Dictionary of Immunology*, pp. 156-158, CRC Press, NY.
Davis et al., (2003), "Immunocytokines: Amplification of Anti-Cancer Immunity," *Cancer Immunol. Immunother.*, 52:297-308.
de la Salle et al., (1996), "FcγR on Human Dendritic Cells," in *Human IgG Receptors*, pp. 39-55, van de Winkel et al. (eds.), R.G. Landes Co.
Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.
Dorai et al., (1991), "Aglycosylated Chimeric Mouse/Human IgG1 Antibody Retains Some Effector Function," *Hybridoma*, 10(2):211-217.
Dorai et al., (1992), "Role of Inter-Heavy and Light Chain Disulfide Bonds in the Effector Functions of Human IgG1," *Molecular Immunology*, 29(12):1487-1491.
Duncan et al., (1988), "The Binding Site for Clq on IgG," *Nature*, 332:738-740.
Ellison et al., (1982), "The Nucleotide Sequence of a Human Immunoglobulin $C\gamma_1$ Gene," *Nucleic Acids Res.*, 10:4071-9.
Fell et al., (1991), "Genetic Construction and Characterization of a Fusion Protein Consisting of a Chimeric F(ab') with Specificity for Carcinomas and Human IL-2," *J. Immunology*, 146(7):2446-2452.
Fell et al., (1992), "Chimeric L6 Anti-Tumor Antibody: Genomic Construction, Expression, and Characterization of the Antigen Binding Site," *J. Biological Chemistry*, 267:15552-15558.
Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.
Fry et al., (2003), "IL-7 Therapy Dramatically Alters Peripheral T-Cell Homeostasis in Normal and SIV-Infected Non-Human Primates," *Blood*, 101:2294-9.

Gan et al., (1999), "Specific Enzyme-Linked Immunosorbent Assays for Quantitation of Antibody-Cytokine Fusion Proteins," *Clinical and Diagnostic Laboratory Immunology*, 6(2):236-42.

Gasson et al., (1984), "Purified Human Granulocyte Macrophage Colony-Stimulating Factor: Direct Action on Neutrophils," *Science*, 226:1339-1342.

Ghetie et al., (1997), "FcRn: The MHC Class I-Related Receptor that is More Than an IgG Transporter," *Immunology Today*, 18(12):592-598.

Gillies et al., (1989), "Expression of Human Anti-Tetanus Toxoid Antibody in Transfected Murine Myeloma Cell," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen Binding and Biological Activities of Engineered Mutant Chimeric Antibodies with Human Tumor Specificities," *Hum. Antibody. Hybridomas*, 1(1):47-54.

Gillies et al., (1991), "Expression of Genetically Engineered Immunoconjugates of Lymphotoxin and a Chimeric Anti-Ganglioside GD2 Antibody," *Hybridoma.*, 10(3):347-56.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Gillies et al., (1992), "Antibody-Targeted Interleukin 2 Stimulates T-Cell Killing of Autologous Tumor Cells," *Proc. Natl. Acad. Sci. USA*, 89:1428-1432.

Gillies et al., (1993), "Biological Activity and In Vivo Clearance of Antitumor Antibody/Cytokine Fusion Proteins," *Bioconjugate Chem.*, 4(3):230-235.

Gillies et al., (1998), "Antibody-IL-12 Fusion Proteins are Effective in SCID Mouse Models of Prostate and Colon Carcinoma Metastases," *J. Immunology*, 160:6195-6203.

Gillies et al., (1999), "Improving the Efficacy of Antibody-Interleukin 2 Fusion Proteins by Reducing Their Interaction with Fc Receptors," *Cancer Research*, 59:2159-2166.

Gillies et al., (2002), "Bi-Functional Cytokine Fusion Proteins for Gene Therapy and Antibody-Targeted Treatment of Cancer," *Cancer Immunol. Immunother.*, 51(8):449-60.

Gillies et al., (2002), "Improved Circulating Half-Line and Efficacy of an Antibody-Interleukin 2 Immunocytokine Based on Reduced Intracellular Proteolysis," *Clin. Cancer Research*, 8(1):210-216.

Goeddel et al., (1986), "Tumor Necrosis Factors: Gene Structure and Biological Activities," *Cold Spring Harb. Symp. Quant. Biol.*, 51:597-609.

Gren et al., (1983), "A New Type of Leukocytic Interferon," English Translation of *Dokl. Akad. Nauk. SSSR.*, 269(4):986-990.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73(8):2081-2085.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Guyre et al., (1997), "Increased Potency of Fc-Receptor-Targeted Antigens," *Cancer Immunol. Immunother.*, 45:146-148.

Halin et al., (2002), "Enhancement of the Antitumor Activity of Interleukin-12 by Targeted Delivery to Neovasculature," *Nature Biotechnology*, 20:264-269.

Hank et al., (1996), "Activation of Human Effector Cells by a Tumor Reactive Recombinant Anti-Ganglioside GD2 Interleukin-2 Fusion Protein (ch14.18-IL2)," *Clin Cancer Research*, 2(12):1951-1959.

Hank et al., (2003), "Determination of Peak Serum Levels and Immune Response to the Humanized Anti-Ganglioside Antibody-Interleukin-2 Immunocytokine," in *Methods in Molecular Medicine, 85: Novel Anticancer Drug Protocols*, Buolamwini et al., (eds.),pp. 123-131, Humana Press Inc., Totowana, NJ.

Harris et al., (1993), "Therapeutic Antibodies—the Coming of Age," *Trends in Biotechnology*, 11:42-44.

Harris, (1995), "Processing of C-Terminal Lysine and Arginine Residues of Proteins Isolated from Mammalian Cell Culture," *J. Chromatography A*, 705:129-134.

Harvill et al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.

Harvill et al., (1996), "In Vivo Properties of an IgG3-IL-2 Fusion Protein: A General Strategy for Immune Potentiation," *J. Immunology*, 157(7):3165-3170.

He et al., (1998), "Humanization and Pharmacokinetics of a Monoclonal Antibody with Specificity for Both E- and P-Selectin," *J. Immunology*, 160:1029-1035.

Henkart, (1985), "Mechanism of Lymphocyte-Mediated Cytotoxicity," *Ann. Rev. Immunol.*, 3:31-58.

Herrmann et al., (1989), "Hematopoietic Responses With Advanced Malignancy Treated With Recombinant Human Granulocyte-Macrophage Colony-Stimulating Factor," *Journal of Clinical Oncology*, 7(2):159-167.

Hezareh et al., (2001), "Effector Function Activities of a Panel of Mutants of a Broadly Neutralizing Antibody against Human Immunodeficiency Virus Type 1," *J. Virology*, 75(24):12161-12168.

Holden et al., (2001), "Augmentation of Antitumor Activity of an Antibody-Interleukin 2 Immunocytokine with Chemotherapeutic Agents," *Clinical Cancer Research*, 7:2862-2869.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675 (XP-002195344).

Hoogenboom et al., (1991), "Construction and Expression of Antibody-Tumor Necrosis Factor Fusion Proteins," *Molecular Immunology*, 28(9):1027-1037.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochem. Biophys. Acta*, 1096(4):345-354 (Abstract).

Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.

Huck et al., (1986), "Sequence of a Human Immunoglobulin Gamma 3 Heavy Chain Constant Region Gene: Comparison With the Other Human Cγ genes," *Nucleic Acids Research*, 14(4):1779-1789.

Hulett et al., (1994), "Molecular Basis of Fc Receptor Function," *Adv. Immunol.*, 57:1127.

Hurn et al., (1980), "Production of Reagent Antibodies," *Methods in Enzymology*, 70: 104-142.

Idusogie et al., (2000), "Mapping of the C1q Binding Site on Rituxan, a Chimeric Antibody with a Human IgG1 Fc," *J. Immunology*, 164(8):4178-4184.

Imboden et al., (2001), "The Level of MHC Class 1 Expression on Murine Adenocarcinoma Can Change the Antitumor Effector Mechanism of Immunocytokine Therapy," *Cancer Research*, 61(4):1500-7.

Isaacs et al., (1998), "Therapy with Monoclonal Antibodies. II. The Contribution of Fcγ Receptor Binding and the Influence of CH1 and CH3 Domains on In Vivo Effector Funcion," *J. Immunol.*, 161:3862-3869.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Jefferis et al., (1990), "Molcular Definition of Interaction Sites on Human IgG for Fc Receptors huFcγR," *Mol. Immunol.*, 27(12):1237-1240.

Jones et al., (2004), "The Development of a Modified Human IFN-α2b Linked to the Fc Portion of Human IgG1 as a Novel Potential Therapeutic for the Treatment of Hepatitis C Virus Infection," *J. Interferon and Cytokine Res.*, 24:560-572.

Jung et al., (1986), "Activation of Human Peripheral Blood Mononuclear Cells by Anti-T3: Killing of Tumor Target Cells Coated with Anti-Target-Anti-T3 Conjugates," *Proc. Natl. Acad. Sci. USA*, 83:4479-4483.
Junghans et al., (1996), "The Protection Receptor of IgG Catabolism is the B2-Microglobulin-Containing Neonatal Intestinal Transport Receptor," *Proc. Natl. Acad. Sci. USA*, 93(11):5512-5516.
Kappel et al., (1992), "Regulating Gene Expression in Transgenic Animals," *Current Opinion in Biotechnology*, 3:548-553.
Karpovsky et al., (1984), "Production of Target-Specific Effector Cells using Hetero-Cross Linked Aggregate Containing Anti-Target Cell and AntiFcγ Receptor Antibodies," *Journal of Experimental Medicine*, 1609(6):1686-1701.
Kendra et al., (1999), "Pharmacokinetics and Stability of the ch14.18-Interleukin-2 Fusion Protein in Mice," *Cancer Immunol. Immunother*., 48:219-229.
Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.
Lode et al., (1999), "Tumor-Targeted IL-2 Amplifies T Cell-Mediated Immune Response Induced by Gene Therapy with Single-Chain IL-12," *Proc. Natl. Acad. Sci. USA*, 96:8591-8596.
Lode et al., (2000), "Amplification of T Cell Mediated Immune Responses by Antibody-Cytokine Fusion Proteins," *Immunological Investigations*, 29(2):117-120.
Lode et al., (2000), "Melanoma Immunotherapy by Targeted IL-2 Depends on CD4(+) T-Cell Help Mediated by CD40/CD40L Interaction," *J. Clin. Invest*., 105(11):1623-30.
Lode et al., (2000), "What To Do With Targeted IL-2," *Drugs of Today*, 36(5):321-336.
MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother*., 19(4):309-316.
Mark et al., (1992), "Expression and Characterization of Hepatocyte Growth Factor Receptor-IgG Fusion Proteins," *Journal of Biological Chemistry*, 267(36):26166-26171.
Martin et al., (2001), "Crystal Structure at 2.8 Å of an FcRn/Heterodimeric Fc Complex: Mechanism of pH-Dependent Binding," *Mol. Cell*., 7(4):867-77.
McMahan et al., (1991), "A Novel IL-1 Receptor, Cloned From B-Cells by Mammalian Expression is Expressed in Many Cell Types," *EMBO J*., 10:2821-32.
Medesan et al., (1997), "Delineation of the Amino Acid Residues Involved in Transcytosis and Catabolism of Mouse IgG1," *J. Immunology*, 158(5):2211-2217.
Metelitsa et al., (2002), "Antidisialoganglioside/Granulocyte Macrophage-Colony-Stimulating Factor Fusion Protein Facilitates Neutrophil Antibody-Dependent Cellular Cytotoxicity and Depends on FcγRII (CD32) and Mac-1 (CD11b/CD18) for Enhanced Effector Cell Adhesion and Azurophil Granule Exocytosis," *Blood*, 99(11):4166-73.
Miyake et al., (1988), "Synthesis of Recombinant Human Single-Chain Urokinase-Type Plasminogen Activator Variants Resistant to Plasmin and Thrombin," *J. Biochem*., 104:643-647.
Morrison et al., (1984), "Chimeric Human Antibody Molecules: Mouse Antigen-Binding Domains with Human Constant Region Domains," *Proc. Natl. Acad. Sci. USA*, 81:6851-5.
Mueller et al., (1990), "Enhancement of Antibody-Dependent Cytotoxicity With A Chimeric Anti-GD2 Antibody," *J. Immunology*, 144(4):1382-1386.
Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA*., 87:5702-5705.
Mueller et al., (1997), "Humanized Porcine VCAM-Specific Monoclonal Antibodies with Chimeric IgG2/G4 Constant Regions Block Human Leukocyte Binding to Porcine Endothelial Cells," *Molecular Immunology*, 34(6):441-452.
Murphy et al., (1986), "Genetic Construction, Expression, and Melanoma-Selective Cytotoxicity of a Diphtheria Toxin-Related β-Melanocyte-Stimulating Hormone Fusion Protein," *Proc. Natl. Acad. Sci. USA*, 83:8258-8262.
Murphy, (1988), "Diphtheria-Related Peptide Hormone Gene Fusions: A Molecular Gene Approach to Chimeric Toxin Development," in *Immunotoxins*, pp. 123-140, Frankel (ed.), Kluwer Acad. Pub.
Naramura et al., (1993), "Therapeutic Potential of Chimeric and Murine Anti-(Epidermal Growth Factor Receptor) Antibodies in a Metastasis Model for Human Melanoma," *Cancer Immuno. Immunother*., 37:343-349.
Naramura et al., (1994), "Mechanisms of Cellular Cytotoxicity Mediated by a Recombinant Antibody-IL2 Fusion Protein Against Human Melanoma Cells," *Immunology Letters*, 39:91-99.
Nastala et al., (1994), "Recombinant IL-2 Adminstration Induces Tumor Regression in Association with IFN-γ Production," *J. Immunol*., 153:1697-706.
Neal et al., (2003), "NXS2 Murine Neuroblastomas Express Increased Levels of MHC Class I Antigens upon Recurrence Following NK-Dependent Immunotherapy," *Cancer Immunol. Immunother*., 53:41-52.
Neal et al., (2004), "Enhanced Activity of Hu14.18-IL2 Immunocytokine against Murine NXS2 Neuroblastoma when Combined with Interleukin-2 Therapy," *Clin. Cancer. Res*., 10:4839-4847.
Nedwin et al., (1985), "Human Lymphotoxin and Tumor Necrosis Factor Genes: Structure, Homology and Chromosomal Localization," *Nucleic Acids Research*, 13(17):6361-6373.
Nelles et al., (1987), "Characterization of Recombinant Human Single Chain Urokinase-Type Plaminogen Activtor Mutants Produced by Site-Specific Mutagenesis of Lysine 158," *J. Biol. Chem*., 262(12):5682-5689.
Neuberger et al., (1984), "Recombinant Antibodies Possessing Novel Effector Functions," *Nature*, 312:604-608.
Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.
Niethammer et al., (2001) "Targeted Interleukin 2 Therapy Enhances Protective Immunity Induced by an Autologous Oral DNA Vaccine against Murine Melanoma," *Cancer Research*, 61(16):6178-84.
Pancook et al., (1996), "Eradication of Established Hepatic Human Neuroblastoma Metastases in Mice with Severe Combined Immunodeficiency by Antibody-Targeted Interleukin-2," *Cancer Immunol. Immunother*., 42(2):88-92.
Pastan et al., (1989), "*Pseudomonas* Exotoxin: Chimeric Toxins," *Journal of Biological Chemistry*, 264(26):15157-15160.
Paul et al., (1988), "Lymphotoxin," *Ann. Rev. Immunol*., 6:407-438.
Pedley et al. (1999), "Enhancement of Antibody-Directed Enzyme Prodrug Therapy in Colorectal Xenografts by an Antivascular Agent," *Cancer Res*., 59:3998-4003.
Perez et al., (1986), "Specific Targeting of Human Peripheral Blood T Cells by Heteroaggregates Containing Anti-T3 Crosslinked to Anti-Target Cell Antibodies," *J. Exp. Med*., 163:166-178.
Poon et al., (1995), "Structure and Function of Several Anti-Dansyl Chimeric Antibodies Formed by Domain Interchanges Between Human IgM and Mouse IgG2b," *J. Biol. Chem*., 270:8571-7.
Reisfeld et al., (1996), "Antibody-Interleukin 2 Fusion Proteins: A New Approach to Cancer Therapy," *J. Clin. Lab. Anal*., 10:160-166.
Reisfeld et al., (1996), "Involvement of B Lymphocytes in the Growth Inhibition of Human Pulmonary Melanoma Metastases in Athymic *nu/nu* Mice by an Antibody-Lymphotoxin Fusion Protein," *Cancer Research*, 56(8):1707-1712.
Reisfeld et al., (1996), "Recombinant Antibody Fusion Proteins for Cancer Immunotherapy," *Current Topics in Microbiology and Immunology*, 213:27-53.
Reisfeld et al., (1997), "Immunocytokines: A New Approach to Immunotherapy of Melanoma," *Melanoma Research*, 7(Supp2):S99-S106.
Robinson et al., (1998), "Optimizing the Stability of Single-Chain Proteins by Linker Length and Composition Mutagenesis," *Proc. Natl. Acad. Sci. USA*, 95:5929-34.
Rosenberg, (1988), "Immunotherapy of Cancer Using Interleukin 2: Current Status and Future Prospects," *Immunology Today*, 9(2):58-62.

Ruehlmann et al., (2001), "MIG (CXCL9) Chemokine Gene Therapy Combines with Antibody-Cytokine Fusion Protein to Suppress Growth and Dissemination of Murine Colon Carcinoma," *Cancer Research*, 61(23):8498-503.
Sabzevari et al., (1994), "A Recombinant Antibody-Interleukin 2 Fusion Protein Suppresses Growth of Hepatic Human Severe Combined Immunodeficiency Mice," *Proc. Natl. Acad. Sci. USA*, 91(20):9626-30.
Sakano et al., (1980), "Two Types of Somatic Recombination are Necessary for the Generation of Complete Immunoglobin Heavy-Chain Genes," *Nature*, 286:676-683.
Schlom (1991), "Monoclonal Antibodies: They're More and Less Than You Think," in *Molecular Foundations of Oncology*, pp. 95-133.
Schnee et al., (1987), "Construction and Expression of a Recombinant Antibody-Targeted Plasminogen Activator," *Proc. Natl. Acad. Sci. USA*, 84:6904-6908.
Senior et al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.
Senter et al., (1988), "Anti-Tumor Effects of Antibody-Alkaline Phosphatase Conjugates in Combination with Etoposide Phosphate," *Proc. Natl. Acad. Sci. USA*, 85(13):4842-4846.
Sharma et al., (1999), "T cell-Derived IL-10 Promotes Lung Cancer Growth by Suppressing Both T cell and APC Function," *Journal of Immunology*, 163:5020-5028.
Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Considerable Within-Species Diversity," *Nucleic Acids Res.*, 16(17):8207-8211.
Shen et al., (1986), "Heteroantibody-Mediated Cytotoxicity: Antibody to the High Affinity Fc Receptor for IgG Mediates Cytotoxicity by Human Monocytes that is Enhanced by Interferon-γ and is Not Blocked by Human IgG," *J. Immunology*, 137(11):3378-3382.
Shin et al., (1990), "Expression and Characterization of an Antibody Binding Specificity Joined to Insulin-Like Growth Factor 1: Potential Applications for Cellular Targeting," *Proc. Natl. Acad. Sci. USA*, 87:5322-5326.
Shinkawa et al., (2003), "The Absence of Fucose But Not the Presence of Galactose or Bisecting N-Acetylglucosamine of Human IgC1 Complex-Type Oligosaccharides Shows the Critical Role of Enhancing Antibody-Dependent Cellular Cytotoxicity," *J. Biol. Chem.*, 278:3466-3473.
Spiekermann et al., (2002), "Receptor-Mediated Immunoglobulin G Transport Across Mucosal Barriers in Adult Life: Functional Expressional of FcRn in the Mammalian Lung," *J. Exp. Med.*, 196:303-310.
Stevenson et al., (1997), "Conjugation of Human Fcγ in Closed-Hinge or Open-Hinge Configuration to Fab'γ and Analogous Ligands," *J. Immunology*, 158:2242-2250.
Storek et al., (2003), "Interleukin-7 Improves CD4 T-Cell Reconstitution After Autologous CD34 Cell Transplantation in Monkeys," *Blood*, 101:4209-18.
Takai, (2002), "Roles of Fc Receptors in Autoimmunity," *Nat. Rev. Immunol.*, 2(8):580-92.
Tao et al., (1989), "Studies of Aglycosylated Chimeric Mouse IgG: Role of Carbohydrate in the Structure and Effector Functions Mediated by the Human IgG Constant Region," *J. Immunology*, 143(8):2595-2601.
Tao et al., (1993), "Structural Features of Human Immunoglobulin G that Determine Isotype-Differences in Complement Activation," *J. Exp. Med.*, 178(2):661-667.
*The Merck Manual of Diagnosis and Therapy, 17th Ed.*, (1999) pp. 990-993 and 1278-1283.
Thommesen et al., (2000), "Lysine 322 in the Human IgG3 CH2 Domain is Crucial for Antibody Dependent Complement Activation," *Mol. Immunol.*, 37(16):995-1004.
Till et al., (1988), "An Assay that Predicts the Ability of Monoclonal Antibodies to Form Potent Ricin A Chain-Containing Immunotoxins," *Cancer Research*, 48(5):1119-1123.
Till et al., (1988), "HIV-Infected Cells are Killed by rCD4-Ricin A Chain," *Science*, 242:1166-1168.
Tiruppathi et al., (1996), "Isolation and Characterization of a Cell Surface Albumin-Binding Protein from Vascular Endothelial Cells," *Proc. Nat. Acad. Sci. USA*, 93:250-4.
Vagliani et al., (1996), "Interleukin 12 Potentiates the Curative Effect of a Vaccine Based on Interleukin 2-Transduced Tumor Cells," *Cancer Research*, 56:467-470.
Verhoeyen et al., (1988), "Reshaping Human Antibodies: Grafting an Antilysozyme Activity," *Science*, 239:1534-36.
Voest et al., (1995), "Inhibition of Angiogenesis in Vivo by Interleukin 12," *J. Natl. Canc. Inst.*, 87:581-6.
Ward et al., (1995), "The Effector Functions of Immunoglobulins: Implications for Therapy," *Therapeutic. Immunology*, 2:77-94.
Weber et al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.
Weitkamp et al., (1973), "Additional Data on the Population Distribution of Human Serum Albumin Genes; Three New Variants," *Ann. Hum. Genet.*, 37:219-26.
Wells, (1990), "Additivity of Mutational Effect in Proteins," *Biochemistry*, 29(37):8509-8517.
Williams et al., (1986), "Production of Antibody-Tagged Enzymes by Myeloma Cells: Application to DNA Polymerase I Klenow Fragment," *Gene*, 43:319-324.
Woof et al., (1986), "Localisation of the Monocyte-Binding Region on Human Immunoglobulin G," *Mol. Immunol.*, 23:319-30.
Wooley et al., (1993), "Influence of a Recombinant Human Soluble Tumor Necrosis Factor Receptor Fc Fusion Protein on Type II Collagen-Induced Arthritis in Mice," *J. Immunology*, 151:6602-6607.
Wysocka et al., (1995), "Interleukin-12 is Required for Interferon-γ Production and Lethality in Lipopolysaccharide-Induced Shock in Mice," *Eur. J. Immunol.*, 25:672-6.
Xiang et al., (1997), "Elimination of Established Murine Colon Carcinoma Metastases by Antibody-Interleukin 2 Fusion Protein Therapy," *Cancer Research*, 57:4948-4955.
Xu et al., (1994), "Residue at Position 331 in the IgG1 and IgG4 CH2 Domains Contributes to Their Differential Ability to Bind and Activate Complement," *J. Biol. Chem.*, 269(5):3469-3474.
Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.
Zheng et al., (1995), "Administration of Noncytolytic IL-10/Fc In Murine Models of Lipopolysaccharide-Induced Septic Shock and Allogeneic Islet Transplantation," *Journal of Immunol.*, 154:5590-5600.
Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.
Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.
International Search Report for International Patent Application No. PCT/EP2004/014555, mailed Feb. 2, 2006 (4 pages).
Written Opinion of the International Searching Authority for International Patent Application No. PCT/EP2004/014555, mailed Feb. 2, 2006 (4 pages).
International Preliminary Report on Patentability for International Patent Application No. PCT/EP2004/014555, mailed Jul. 13, 2006 (5 pages).
"Bos Taurus IL-7 mRNA, complete cds." EMBL Database, EBI accession No. AF348422, Dec. 4, 2002.
"Ovis aries interleukin-7 (IL-7), complete cds." EMBL Database, EBI accession No. U10089, Jun. 8, 1994.
Alpdogan et al., (2005), "IL-7 and IL-15: therapeutic cytokines for immunodeficiency," *Trends in Immunology*, 26(1):56-64.
Chamow et al., (1996), "Immunoadhesins: Principles and Applications," *Trends in Biotechnology*, 14(2):52-60.
Colman et al. (1994), "Effects of Amino Acid Sequence Changes on Antibody-Antigen Interactions," *Res. Immunol.*, 145:33-36.

Cosenza et al., "Comparative Model Building of Interleukin-7 using Interleukin-4 as a Template: A Structural Hypothesis that Displays Atypical Surface Chemistry in Helix D Important for Receptor Activation," *Protein Science*, 9:916-926, (2000).

Cosenza et al., (1997), "Disulfide Bond Assignment in Human Interleukin-7 by Matrix-assisted Laser Desorpotion/Ionization Mass Spectroscopy and Site-directed Cysteine to Serine Mutational Analysis," *The Journal of Bio. Chem.*, 272(52): 32995-33000.

Couto et al., (1994) "Humanization of KC4G3, an Anti-Human Carcinoma Antibody," *Hybridoma*, 3:215-219.

Database Uniprot, (Jul. 21, 1986), Database Accession No. P01859.

Jefferis et al., (1998), "IgG-Fc-Mediated Effector Functions: Molecular Definition of Interaction Sites for Effector Ligands and the Role of Glycosylation," *Immunological Reviews*, 163:59-76.

Kroemer et al., (1998), "Comparison of the 3D Models of Four Different Human IL-7 Isoforms with Human and Murine IL-7," *Protein Engineering*, 11(1): 31-40.

Kroemer et al., (1996), "Homology Modeling Study of the Human Interleukin-7 Receptor Complex," *Protein Engineering*, 9(12):1135-1142.

Kroemer et al. (1996), "Prediction of the Three-Dimensional Structure of Human Interleukin-7 by Homology Modeling," *Protein Engineering*, 9(6): 493-498.

Lo et al., (2006), "huBC-IL2, An Immunocytokine which Targets EDB-Containing Oncofetal Fibronectin in Tumors and Tumor Vasculature, Shows Potent Anti-Tumor Activity in Human Tumor Models," *Cancer Immunol. Immunother.*, 56:446-457.

Lund et al., (1993), "Control of IgG/Fc Glycosylation: A Comparison of Oligosaccharides from Chimeric Human/Mouse and Mouse Subclass Immunoglobulin Gs," *Mol. Immunol.*, 30(8):741-748.

Mateo et al., (2000), "Removal of Amphipathic Epitopes from Genetically Engineered Antibodies: Production of Modified Immunoglobulins with Reduced Immunogenicity," *Hybridoma*, 19(6):463-471.

Michaelsen et al., (1977), "Primary Structure of the Hinge Region of Human IgG3," *J. Biol. Chem.*, 252(3):883-889.

Olosz et al., (2002), "Structural Basis For Binding Multiple Ligands by the Common Cytokine Receptor γ-Chain," *The Journal of Bio. Chem.*, 277(14): 12047-12052.

Padlan et al., (1991), "A Possible Procedure for Reducing the Immunogenicity of Antibody Variable Domains while Preserving Their Ligand Binding Properties," *Mol. Immunol.*, 28:489-498.

Ravetch, (1997), "Fc Receptors," *Curr. Opin. Immunol.*, 9:121-125.

Storek et al., (2003), "Interleukin-7 improves CD4 T-cell reconstitution after autologous CD34 cell transplantation in monkeys," *Blood*, 101(10):4209-4218.

Tao et al., (1991), "The Differential Ability of Human IgG1 and IgG4 to Activate Complement Is Determined by the COOH-terminal Sequence of the $C_H2$ Domain," *J. Exp. Med.*, 173:1025-1028.

vanderSpek et al., "Structure function analysis of interleukin 7: requirement for an aromatic ring at position 143 of helix D," *Cytokine*, 17(5): 227-33 (2002).

Vitetta et al., (1987), "Redesigning Nature's Poisons to Create Anti-Tumor Reagents," *Science*, 238:10981104.

Yokota et al., (1986), "Isolation and Characterization of a Human Interleukin cDNA Clone, Homologous to Mouse B-Cell Stimulatory Factor 1, that Expresses B-Cell- and T-Cell-Stimulating Activities," *Proc. Natl. Acad. Sci. USA*, 83:5894-5898.

* cited by examiner

Human IL-7

MFHVSFRYIFGLPPLILVLLPVASSDCDIEGKDGKQYESVLMVSIDQLLDSMKEIGSNC
LNNEFNFFKRHICDANKEGMFLFRAARKLRQFLKMNSTGDFDLHLLKVSEGTTILLNCT
GQ*VKGRKPAALGEAQPTKSL*EENKSLKEQKKLNDLCFLKRLLQEIKTCWNKILMGTKEH
(SEQ ID NO:1)

FIG 1

Cow IL-7

MFHVSFRYIFGIPPLILVLLPVASSDCDISGRDGGAYQNVLMVNIDDLDNMINFDSNCL
NNEPNFFKKHSCDDNKEASFLNRASRKLRQFLKMNISDDFKLHLSTVSQGTLTLLNCTS
KGKGRKPPSLSEAQPTKNLEENKSSREQKKQNDLCFLKILLQKIK TCWNKILRGIKEH
(SEQ ID NO:2)

FIG 2

Sheep IL-7

MFHVSFRYIFGIPPLILVLLPVASSDCDFSGKDGGAYQNVLMVSIDDLDNMINFDSNCL
NNEPNFFKKHSCDDNKEASFLNRAARKLKQFLKMNISDDFKLHLSTVSQGTLTLLNCTS
KGKGRKPPSLGEAQPTKNLEENKSLKEQRKQNDLCFLKILLQKIKTCWNKILRGITEH
(SEQ ID NO:3)

FIG 3

Human Fcγ1-IL-7

EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSATATPGADCDI
EGKDGKQYESVLMVSIDQLLDSMKEIGSNCLNNEFNFFKRHICDANKEGMFLFRAARKL
RQFLKMNSTGDFDLHLLKVSEGTTILLNCTGQVKGRKPAALGEAQPTKSLEENKSLKEQ
KKLNDLCFLKRLLQEIKTCWNKILMGTKEH (SEQ ID NO:4)

FIG 4

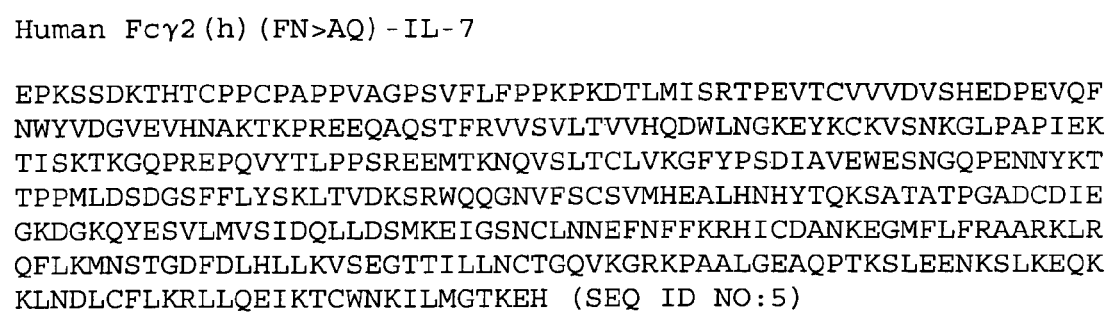

Human Fcγ2(h)(FN>AQ)-IL-7

EPKSSDKTHTCPPCPAPPVAGPSVFLFPPKPKDTLMISRTPEVTCVVVDVSHEDPEVQF
NWYVDGVEVHNAKTKPREEQAQSTFRVVSVLTVVHQDWLNGKEYKCKVSNKGLPAPIEK
TISKTKGQPREPQVYTLPPSREEMTKNQVSLTCLVKGFYPSDIAVEWESNGQPENNYKT
TPPMLDSDGSFFLYSKLTVDKSRWQQGNVFSCSVMHEALHNHYTQKSATATPGADCDIE
GKDGKQYESVLMVSIDQLLDSMKEIGSNCLNNEFNFFKRHICDANKEGMFLFRAARKLR
QFLKMNSTGDFDLHLLKVSEGTTILLNCTGQVKGRKPAALGEAQPTKSLEENKSLKEQK
KLNDLCFLKRLLQEIKTCWNKILMGTKEH (SEQ ID NO:5)

FIG 5

Human FCγ1(linker1)-IL-7

EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSATATPGAGGGG
SGGGGSGGGSDCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKGRKPAALGEAQ
PTKSLEENKSLKEQKKLNDLCFLKRLLQEIKTCWNKILMGTKEH (SEQ ID NO:6)

FIG 6

Human Fcγ1(YN>AQ)(linker2)-IL-7

EPKSSDKTHTCPPCPAPELLGGPSVFLFPPKPKDTLMISRTPEVTCVVVDVSHEDPEVK
FNWYVDGVEVHNAKTKPREEQAQSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSATATPGAGGGG
SGGGGDCDIEGKDGKQYESVLMVSIDQLLDSMKEIGSNCLNNEFNFFKRHICDANKEGM
FLFRAARKLRQFLKMNSTGDFDLHLLKVSEGTTILLNCTGQVKGRKPAALGEAQPTKSL
EENKSLKEQKKLNDLCFLKRLLQEIKTCWNKILMGTKEH (SEQ ID NO:7)

FIG 7

Human Fcγ1(YN>AQ,d)(linker2)-IL-7

EPKSSDKTHTCPPCPAPELLGGPSVFLFPPKPKDTLMISRTPEVTCVVVDVSHEDPEVK
FNWYVDGVEVHNAKTKPREEQAQSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSATATPGGGGSG
GGGDCDIEGKDGKQYESVLMVSIDQLLDSMKEIGSNCLNNEFNFFKRHICDANKEGMFL
FRAARKLRQFLKMNSTGDFDLHLLKVSEGTTILLNCTGQVKGRKPAALGEAQPTKSLEE
NKSLKEQKKLNDLCFLKRLLQEIKTCWNKILMGTKEH (SEQ ID NO:8)

FIG 8

Human Fcγ1

GAGCCCAAATCTTCTGACAAAACTCACACATGCCCACCGTGCCCAGGTAAGCCAGCCCA
GGCCTCGCCCTCCAGCTCAAGGCGGGACAGGTGCCCTAGAGTAGCCTGCATCCAGGGAC
AGGCCCCAGCCGGGTGCTGACACGTCCACCTCCATCTCTTCCTCAGCACCTGAACTCCT
GGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGGGAGGA
GCAGTACAACAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCCCCCATCGAG
AAAACCATCTCCAAAGCCAAAGGTGGGACCCGTGGGGTGCGAGGGCCACATGGACAGAG
GCCGGCTCGGCCCACCCTCTGCCCTGAGAGTGACCGCTGTACCAACCTCTGTCCCTACA
GGGCAGCCCCGAGAACCACAGGTGTACACCCTGCCCCCATCACGGGAGGAGATGACCAA
GAACCAGGTCAGCCTGACCTGCCTGGTCAAAGGCTTCTATCCCAGCGACATCGCCGTGG
AGTGGGAGAGCAATGGGCAGCCGGAGAACAACTACAAGACCACGCCTCCCGTGCTGGAC
TCCGACGGCTCCTTCTTCCTCTATAGCAAGCTCACCGTGGACAAGAGCAGGTGGCAGCA
GGGGAACGTCTTCTCATGCTCCGTGATGCATGAGGCTCTGCACAACCACTACACGCAGA
AGAGCGCCACCGCGACCCCGGGCGCC (SEQ ID NO:22)

FIG 9

Human Fcγ1(YN>AQ)

GAGCCCAAATCTTCTGACAAAACTCACACATGCCCACCGTGCCCAGGTAAGCCAGCCCA
GGCCTCGCCCTCCAGCTCAAGGCGGGACAGGTGCCCTAGAGTAGCCTGCATCCAGGGAC
AGGCCCCAGCCGGGTGCTGACACGTCCACCTCCATCTCTTCCTCAGCACCTGAACTCCT
GGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGGGAGGA
GCAGGCCCAGAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCCCCCATCGAG
AAAACCATCTCCAAAGCCAAAGGTGGGACCCGTGGGGTGCGAGGGCCACATGGACAGAG
GCCGGCTCGGCCCACCCTCTGCCCTGAGAGTGACCGCTGTACCAACCTCTGTCCCTACA
GGGCAGCCCCGAGAACCACAGGTGTACACCCTGCCCCCATCACGGGAGGAGATGACCAA
GAACCAGGTCAGCCTGACCTGCCTGGTCAAAGGCTTCTATCCCAGCGACATCGCCGTGG
AGTGGGAGAGCAATGGGCAGCCGGAGAACAACTACAAGACCACGCCTCCCGTGCTGGAC
TCCGACGGCTCCTTCTTCCTCTATAGCAAGCTCACCGTGGACAAGAGCAGGTGGCAGCA
GGGGAACGTCTTCTCATGCTCCGTGATGCATGAGGCTCTGCACAACCACTACACGCAGA
AGAGCGCCACCGCGACCCCGGGCGCC (SEQ ID NO:21)

FIG 10

Human Fcγ2(h)

GAGCCCAAATCTTCTGACAAAACTCACACATGCCCACCGTGCCCAGGTAAGCCAGCCCA
GGCCTCGCCCTCCAGCTCAAGGCGGGACAGGTGCCCTAGAGTAGCCTGCATCCAGGGAC
AGGCCCCAGCTGGGTGCTGACACGTCCACCTCCATCTCTTCCTCAGCACCACCTGTGGC
AGGACCGTCAGTCTTCCTCTTCCCCCCAAAACCCAAGGACACCCTCATGATCTCCCGGA
CCCCTGAGGTCACGTGCGTGGTGGTGGACGTGAGCCACGAAGACCCCGAGGTCCAGTTC
AACTGGTACGTGGACGGCGTGGAGGTGCATAATGCCAAGACAAAGCCACGGGAGGAGCA
GTTCAACAGCACGTTCCGTGTGGTCAGCGTCCTCACCGTTGTGCACCAGGACTGGCTGA
ACGGCAAGGAGTACAAGTGCAAGGTCTCCAACAAAGGCCTCCCAGCCCCCATCGAGAAA
ACCATCTCCAAAACCAAAGGTGGGACCCGCGGGGTATGAGGGCCACATGGACAGAGGCC
GGCTCGGCCCACCCTCTGCCCTGAGAGTGACCGCTGTACCAACCTCTGTCCCTACAGGG
CAGCCCCGAGAACCACAGGTGTACACCCTGCCCCCATCACGGGAGGAGATGACCAAGAA
CCAGGTCAGCCTGACCTGCCTGGTCAAAGGCTTCTACCCCAGCGACATCGCCGTGGAGT
GGGAGAGCAATGGGCAGCCGGAGAACAACTACAAGACCACACCTCCCATGCTGGACTCC
GACGGCTCCTTCTTCCTCTACAGCAAGCTCACCGTGGACAAGAGCAGGTGGCAGCAGGG
GAACGTCTTCTCATGCTCCGTGATGCATGAGGCTCTGCACAACCACTACACACAGAAGA
GCGCCACCGCGACCCCGGGCGCC (SEQ ID NO:20)

FIG 11

Human Fcγ2(h)(FN>AQ)

GAGCCCAAATCTTCTGACAAAACTCACACATGCCCACCGTGCCCAGGTAAGCCAGCCCA
GGCCTCGCCCTCCAGCTCAAGGCGGGACAGGTGCCCTAGAGTAGCCTGCATCCAGGGAC
AGGCCCCAGCTGGGTGCTGACACGTCCACCTCCATCTCTTCCTCAGCACCACCTGTGGC
AGGACCGTCAGTCTTCCTCTTCCCCCCAAAACCCAAGGACACCCTCATGATCTCCCGGA
CCCCTGAGGTCACGTGCGTGGTGGTGGACGTGAGCCACGAAGACCCCGAGGTCCAGTTC
AACTGGTACGTGGACGGCGTGGAGGTGCATAATGCCAAGACAAAGCCACGGGAGGAGCA
GGCCCAGAGCACGTTCCGTGTGGTCAGCGTCCTCACCGTTGTGCACCAGGACTGGCTGA
ACGGCAAGGAGTACAAGTGCAAGGTCTCCAACAAAGGCCTCCCAGCCCCCATCGAGAAA
ACCATCTCCAAAACCAAAGGTGGGACCCGCGGGGTATGAGGGCCACATGGACAGAGGCC
GGCTCGGCCCACCCTCTGCCCTGAGAGTGACCGCTGTACCAACCTCTGTCCCTACAGGG
CAGCCCCGAGAACCACAGGTGTACACCCTGCCCCCATCACGGGAGGAGATGACCAAGAA
CCAGGTCAGCCTGACCTGCCTGGTCAAAGGCTTCTACCCCAGCGACATCGCCGTGGAGT
GGGAGAGCAATGGGCAGCCGGAGAACAACTACAAGACCACACCTCCCATGCTGGACTCC
GACGGCTCCTTCTTCCTCTACAGCAAGCTCACCGTGGACAAGAGCAGGTGGCAGCAGGG
GAACGTCTTCTCATGCTCCGTGATGCATGAGGCTCTGCACAACCACTACACACAGAAGA
GCGCCACCGCGACCCCGGGTGCA (SEQ ID NO:19)

FIG 12

IL-7 FUSION PROTEINS

RELATED APPLICATIONS

This application claims priority to and the benefit of U.S. Provisional Application No. 60/533,406, filed Dec. 30, 2003, the entire disclosure of which is incorporated herein by reference.

FIELD OF THE INVENTION

The invention relates to interleukin-7 (IL-7) fusion proteins, methods of their production and uses thereof. The proteins of the invention are particularly useful in treating disorders accompanied by immune deficiencies and particularly diseases which involve T-cell deficiencies.

BACKGROUND OF THE INVENTION

A variety of disorders and therapies involve a deficiency of immune cells. For example, HIV infection results in a loss of CD4+ T-cells, while therapies such as chemotherapy and radiation therapy generally result in a loss of a wide variety of blood cells. Attempts have been made to provide specific protein drugs that can replenish specific types of immune cells that are lost as a result of a disease or therapy. For example, in cancer chemotherapy, erythropoietin is used to replenish red blood cells, granulocyte colony-stimulating factor (G-CSF) is used to replenish neutrophils, and granulocyte macrophage colony stimulating factor (GM-CSF) is used to replenish granulocytes and macrophages. These protein drugs, although beneficial, have relatively short serum half-lives such that immune cell replenishment is often insufficient. Moreover, no specific treatment is currently in clinical use to specifically stimulate T or B-cell development, even though loss of these cells as a result of disease or after certain myeloablative treatments is know to be particularly deleterious to a patient's health. Thus, there exists a need in the art to develop immune system stimulators and restoratives, particularly of lymphocytes, that have extended serum half-lives.

SUMMARY OF THE INVENTION

The present invention is directed to interleukin-7 (IL-7) fusion proteins which have improved biological properties compared to corresponding wild-type IL-7 proteins. Moreover, the present invention is based, in part, on the finding that IL-7 fusion proteins having particular structural features have improved biological properties compared to wild-type recombinant IL-7.

Accordingly, in one aspect, the invention features a fusion protein including a first portion comprising an immunoglobulin (Ig) chain and a second portion comprising interleukin-7 (IL-7), wherein the IL-7 fusion protein has an increased biological activity, such as an extended-serum half-life or in promoting the survival or expansion of immune cells, as compared to wild-type IL-7.

In one embodiment, the invention features a fusion protein including a first portion including an Ig chain and a second portion including IL-7, wherein the amino acid residues at positions 70 and 91 of IL-7 are glycosylated and the amino acid residue at position 116 of IL-7 is non-glycosylated. Throughout this document, amino acid positions of IL-7 refer to the corresponding positions in the mature, human IL-7 sequence. In one embodiment, the amino acid residue at position 116 of IL-7 is asparagine. In another embodiment, the amino acid residue at position 116 of IL-7 is altered such that it does not serve as a glycosylation site. In one embodiment, the IL-7 moiety comprises disulfide bonds between Cys2 and Cys92, Cys34 and Cys129, and Cys47 and Cys141 of IL-7.

In another embodiment, the invention includes a fusion protein including a first portion including an Ig chain and a second portion including IL-7, wherein the IL-7 comprises disulfide bonding between Cys2 and Cys92, Cys34 and Cys129, and Cys47 and Cys141 of IL-7. In one embodiment, the amino acid residue at position 116 of IL-7 is non-glycosylated. In another embodiment, the amino acid residue at position 116 of IL-7 is asparagine or is altered such that it does not serve as a glycosylation site. In another embodiment, the amino acid residues at positions 70 and 91 of IL-7 are glycosylated.

The Ig chain is generally an intact antibody or portion thereof, such as an Fc region. The Ig chain of the IL-7 fusion protein can be derived from any known Ig isotype and can include at least a portion of one or more constant domains. For example, the constant domain can be selected from the group consisting of a CH1 region, a hinge region, a CH2 region, and a CH3 region. In one embodiment, the Ig moiety includes a hinge region, a CH2 region and a CH3 region. The Ig chain is optionally connected to the IL-7 portion by a linker.

Ig moieties of a single antibody isotype, such as IgG1 or IgG2, and hybrid Ig moieties are permitted in the present invention. For example, in one embodiment, the Ig moiety includes a hinge region derived from one isotype (i.e. IgG2) and a CH region from another isotype (i.e. IgG1). An Ig chain including an Fc portion of IgG1 can advantageously be modified to include the mutations Asn297Gln and Tyr296Ala. Furthermore, an Ig chain including an Fc portion of IgG2 can be advantageously modified to include the mutations Asn297Gln and Phe296Ala.

The IL-7 portion of the IL-7 fusion protein described above may comprise the mature portion of the IL-7 portion. In one embodiment, the IL-7 portion can further include a deletion, such as an internal deletion. In one example, IL-7 can include an eighteen amino acid deletion of amino acids 96 to 114 of SEQ ID NO:1.

In other embodiments, the invention includes purified nucleic acids encoding the IL-7 fusion proteins described above and cultured host cells including these nucleic acids.

In another aspect, the invention includes a method of preparing an IL-7 fusion protein including expressing in a host cell the nucleic acid described above and harvesting the fusion protein.

In another aspect, the invention includes a composition such as a pharmaceutical composition which includes the fusion protein described above.

In another aspect, the invention includes a method of treating a patient by administering Fc-IL-7 fusion proteins.

BRIEF DESCRIPTION OF THE DRAWINGS

FIG. 1 depicts the amino acid sequence of human IL-7 (SEQ ID NO:1). The signal sequence is shown in bold. Also depicted in bold and italics is a stretch of eighteen amino acids which can be deleted from the IL-7 sequence.

FIG. 2 depicts the amino acid sequence of cow IL-7 (SEQ ID NO:2). The signal sequence is shown in bold.

FIG. 3 depicts the amino acid sequence of sheep IL-7 (SEQ ID NO:3). The signal sequence is shown in bold.

FIG. 4 depicts the amino acid sequence of mature human Fcγ1-IL-7 (SEQ ID NO:4).

FIG. 5 depicts the amino acid sequence of mature human Fcγ2(h)(FN>AQ)-IL-7 (SEQ ID NO:5).

FIG. 6 depicts the amino acid sequence of mature human Fcγ1(linker1)-IL-7 (SEQ ID NO:6).

FIG. 7 depicts the amino acid sequence of mature human Fcγ1(YN>AQ)(linker2)-IL-7 (SEQ ID NO:7).

FIG. 8 depicts the amino acid sequence of mature human Fcγ1(YN>AQ,d)(linker2)-IL-7 (SEQ ID NO:8).

FIG. 9 depicts the nucleic acid sequence for the Fc region of human Fcγ1-IL-7 (SEQ ID NO:22).

FIG. 10 depicts the nucleic acid sequence for the Fc region of human Fcγ1(YN>AQ)-IL-7 (SEQ ID NO:21).

FIG. 11 is the nucleic acid sequence for the Fc region of human Fcγ2(h)-IL-7 (SEQ ID NO:20).

FIG. 12 is the nucleic acid sequence for the Fc region of human Fcγ2(h) (FN>AQ)-IL-7 (SEQ ID NO:19)

DETAILED DESCRIPTION OF THE INVENTION

Figure 13:
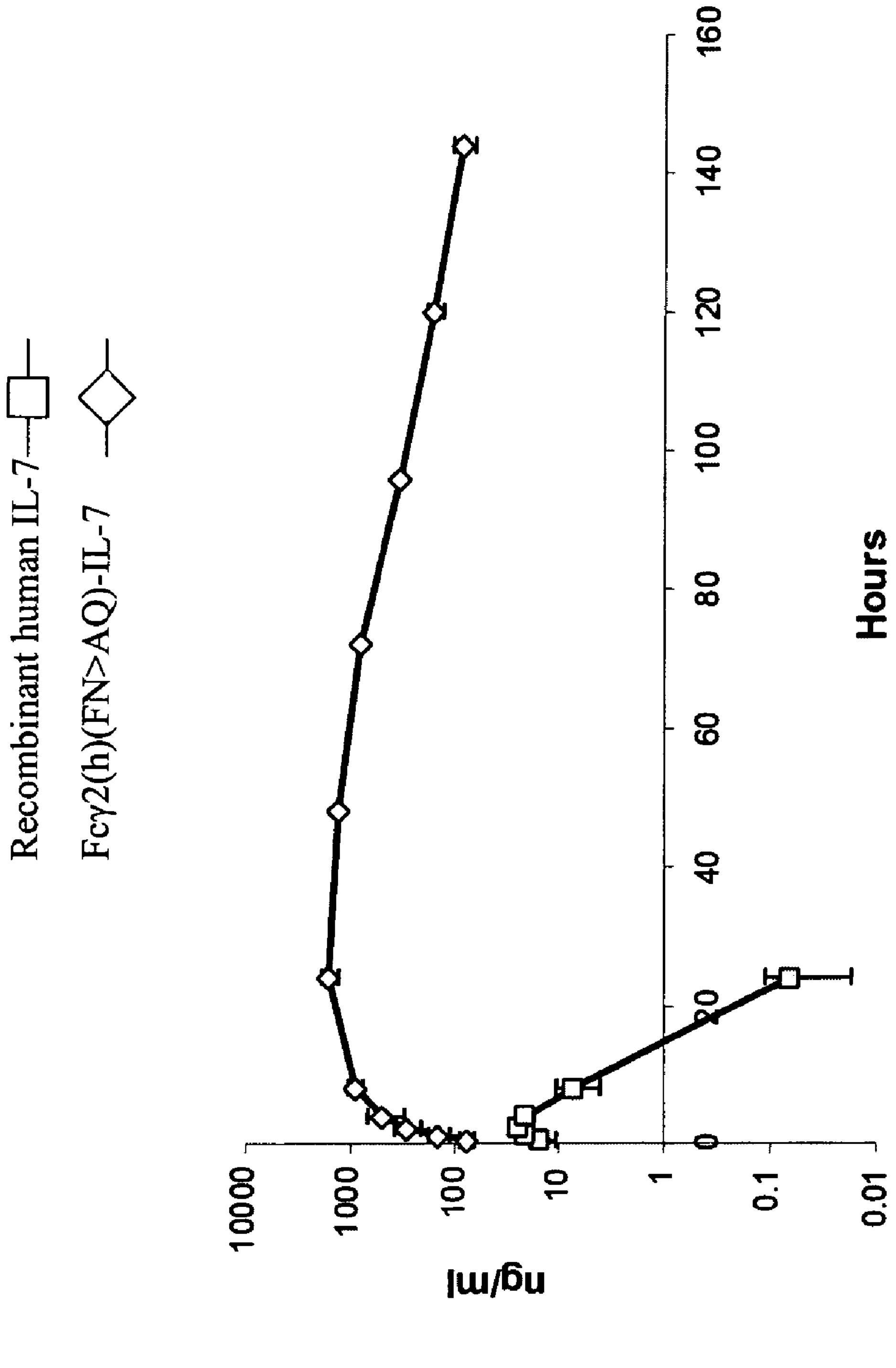
FIG. 13 is a graphical representation of the pharmacokinetic profile of recombinant human IL-7 (open squares) and the fusion protein Fcγ2(h)(FN>AQ)-IL-7 (open diamonds) of Example 7. The serum concentration of the administered IL-7 fusion proteins (in ng/ml) was measured over time (in hours).

The invention provides IL-7 fusion proteins that have enhanced biological activity compared to wild-type IL-7 proteins. In particular, the invention provides IL-7 fusion proteins that include an immunoglobulin (Ig) portion. These Ig-IL-7 fusion proteins have enhanced biological activity, such as extended serum half-life as compared to the wild type IL-7 proteins, which makes them suitable for use in the treatment of conditions accompanied by immune cell deficiencies such as lymphocyte deficiencies.

The invention is further based in part on the finding that IL-7 fusion proteins that have particular structural characteristics also have enhanced biological properties. While the amino acid sequence of mammalian IL-7 is well known, information about the structure of eukaryotically derived IL-7 proteins, including, for example, how the protein folds and the effects of its predicted N-linked glycosylation sites on its biological activity, remain ill-defined. For example, human IL-7 protein has a cysteine at positions 2, 34, 47, 92, 129, and 141 of the mature protein and three potential N-linked glycosylation sites at positions asparagine (Asn) 70, Asn91, and Asn116. However, the precise structure of IL-7 synthesized under eukaryotic conditions is unknown.

The present invention includes IL-7 fusion proteins having particular structural forms and enhanced biological activity. For example, IL-7 fusion proteins having the disulfide bonding pattern of Cys2-Cys92, Cys34-Cys129 and Cys47-141 are more active in vivo than a wild-type recombinant IL-7 protein.

Moreover, the invention provides a form of an IL-7 fusion protein in which only two of the three potential N-linked glycosylation sites of IL-7 are glycosylated. Specifically, Asn70 and Asn91 of the mature protein are glycosylated, while the predicted N-linked glycosylation site at IL-7 Asn116 is not glycosylated. Such an IL-7 fusion protein is more active in vivo than a wild-type recombinant IL-7.

The invention also includes IL-7 fusion proteins wherein the IL-7 moiety contains a deletion and which retain comparable activity compared to the corresponding unmodified IL-7 fusion proteins. For example, the invention provides a form of Ig-IL-7 in which the IL-7 moiety contains an eighteen amino acid internal deletion corresponding to the sequence VKGRKPAALGEAQPTKSL (SEQ ID NO:9).

Interleukin-7 Fusion Proteins

Typically, the IL-7 protein portion is fused to a carrier protein. In one embodiment, the carrier protein is disposed towards the N-terminus of the fusion protein and the IL-7 protein is disposed towards the C-terminus. In another embodiment, the IL-7 fusion protein is disposed towards the N-terminus of the fusion protein and the carrier protein is disposed towards the C-terminus.

As used herein, the term "interleukin-7" or "IL-7" mean IL-7 polypeptides and derivatives and analogs thereof having substantial amino acid sequence identity to wild-type mature mammalian IL-7s and substantially equivalent biological activity, e.g., in standard bioassays or assays of IL-7 receptor binding affinity. For example, IL-7 refers to an amino acid sequence of a recombinant or non-recombinant polypeptide having an amino acid sequence of: i) a native or naturally-occurring allelic variant of an IL-7 polypeptide, ii) a biologically active fragment of an IL-7 polypeptide, iii) a biologically active polypeptide analog of an IL-7 polypeptide, or iv) a biologically active variant of an IL-7 polypeptide. IL-7 polypeptides of the invention can be obtained from any species, e.g., human, cow or sheep. IL-7 nucleic acid and amino acid sequences are well known in the art. For example, the human IL-7 amino acid sequence has a Genbank accession number of NM 000880 (SEQ ID NO:1) and is shown in FIG. 1; the mouse IL-7 amino acid sequence has a Genbank accession number of NM 008371; the rat IL-7 amino acid sequence has a Genbank accession number of AF 367210; the cow IL-7 amino acid sequence has a Genbank accession number of NM 173924 (SEQ ID NO:2) and is shown in FIG. 2; and the sheep IL-7 amino acid sequence has a Genbank accession number of U10089 (SEQ ID NO:3) and is shown in FIG. 3. The signal sequence for each of the polypeptide species is shown in bold in each of the figures and is typically not included where the IL-7 portion is fused C-terminal to the carrier protein.

A "variant" of an IL-7 protein is defined as an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted or deleted without abolishing biological activity can be found using computer programs well known in the art, for example software for molecular modeling or for producing alignments. The variant IL-7 proteins included within the invention include IL-7 proteins that retain IL-7 activity. IL-7 polypeptides which also include additions, substitutions or deletions are also included within the invention as long as the proteins retain substantially equivalent biological IL-7 activity. For example, truncations of IL-7 which retain comparable biological activity as the full length form of the IL-7 protein are included within the invention. The activity of the IL-7 protein can be measured using in vitro cellular proliferation assays such as described in Example 6 below. The activity of IL-7 variants of the invention maintain biological activity of at least 10%, 20%, 40%, 60%, but more preferably 80%, 90%, 95% and even more preferably 99% as compared to wild type IL-7.

Variant IL-7 proteins also include polypeptides that have at least about 70%, 75%, 80%, 85%, 90%, 92%, 95%, 96%, 97%, 98%, 99%, or more sequence identity with wild-type IL-7. To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The percent identity between the two sequences is a function of the number of identical positions shared by the sequences (i.e., % homology=# of identical positions/total # of positions.times.100). The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs of Altschul, et al. (1990) *J. Mol. Biol.* 215:403-10. BLAST nucleotide searches can be performed with the NBLAST program, score=100, wordlength=12. BLAST protein searches can be performed with the XBLAST program, score=50, wordlength=3. To obtain gapped alignments for comparison purposes, Gapped BLAST can be utilized as described in Altschul et al., (1997) *Nucleic Acids Research* 25(17):3389-3402. When utilizing BLAST and Gapped BLAST programs, the default parameters of the respective programs (e.g., XBLAST and NBLAST) can be used.

Potential T-cell of B-cell epitopes in the IL-7 moiety can be removed or modified in the Fc-IL-7 fusion proteins of the invention. Exemplary deimmunized IL-7 moieties are disclosed in U.S. Provisional Patent Application No. 60/634,470.

Carrier Protein

The carrier protein can be any moiety covalently fused to the IL-7 protein. In one embodiment, the carrier protein is albumin, for example, human serum albumin. In another embodiment, the carrier protein is an immunoglobulin (Ig) moiety, such as an Ig heavy chain. The Ig chain may be derived from IgA, IgD, IgE, IgG, or IgM. According to the invention, the Ig moiety may form an intact antibody and may direct the IL-7 fusion protein to specific target sites in the body. Fusion proteins making use of antibody targeting are known to those in the art. In another embodiment, the carrier Ig moiety further comprises an Ig light chain.

In one embodiment, the Ig moiety comprises an Fc region. As used herein, "Fc portion" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in any combination. In the present invention, the Fc portion typically includes at least a CH2 domain. For example, the Fc portion can include hinge-CH2—CH3. Alternatively, the Fc portion can include all or a portion of the hinge region, the CH2 domain and/or the CH3 domain and/or the CH4 domain.

The constant region of an immunoglobulin is responsible for many important antibody functions including Fc receptor (FcR) binding and complement fixation. There are five major classes of heavy chain constant region, classified as IgA, IgG, IgD, IgE, and IgM. For example, IgG is separated into four γ subclasses: γ1, γ2, γ3, and γ4, also known as IgG1, IgG2, IgG3, and IgG4, respectively.

IgG molecules interact with multiple classes of cellular receptors including three classes of Fcγreceptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR). Similarly, the serum half-life of immunoglobulin fusion proteins is also influenced by the ability to bind to such receptors (Gillies et al., (1999) *Cancer Res.* 59:2159-66). Compared to those of IgG1, CH2 and CH3 domains of IgG2 and IgG4 have biochemically undetectable or reduced binding affinity to Fc receptors. It has been reported that immunoglobulin fusion proteins containing CH2 and CH3 domains of IgG2 or IgG4 had longer serum half-lives compared to the corresponding fusion proteins containing CH2 and CH3 domains of IgG1 (U.S. Pat. No. 5,541,087; Lo et al., (1998) *Protein Engineering,* 11:495-500). Accordingly, in certain embodiments of the invention, preferred CH2 and CH3 domains are derived from an antibody isotype with reduced receptor binding affinity and effector functions, such as, for example, IgG2 or IgG4. More preferred CH2 and CH3 domains are derived from IgG2.

The hinge region is normally located C-terminal to the CH1 domain of the heavy chain constant region. In the IgG isotypes, disulfide bonds typically occur within this hinge region, permitting the final tetrameric antibody molecule to form. This region is dominated by prolines, serines and threonines. When included in the present invention, the hinge region is typically at least homologous to the naturally-occurring immunoglobulin region that includes the cysteine residues to form disulfide bonds linking the two Fc moieties. Representative sequences of hinge regions for human and mouse immunoglobulins are known in the art and can be found in Borrebaeck, ed., (1992) *Antibody Engineering, A Practical Guide*, W. H. Freeman and Co. Suitable hinge regions for the present invention can be derived from IgG1, IgG2, IgG3, IgG4, and other immunoglobulin classes.

The IgG1 hinge region has three cysteines, the second and third of which are involved in disulfide bonds between the two heavy chains of the immunoglobulin. These same two cysteines permit efficient and consistent disulfide bonding of an Fc portion. Therefore, a preferred hinge region of the present invention is derived from IgG1, more preferably from human IgG1, wherein the first cysteine is preferably mutated to another amino acid, preferably serine.

The IgG2 isotype hinge region has four disulfide bonds that tend to promote oligomerization and possibly incorrect disulfide bonding during secretion in recombinant systems. A suitable hinge region can be derived from an IgG2 hinge; the first two cysteines are each preferably mutated to another amino acid.

The hinge region of IgG4 is known to form interchain disulfide bonds inefficiently. However, a suitable hinge region for the present invention can be derived from the IgG4 hinge region, preferably containing a mutation that enhances correct formation of disulfide bonds between heavy chain-derived moieties (Angal et al. (1993) *Mol. Immunol.,* 30:105-8).

In accordance with the present invention, the Fc portion can contain CH2 and/or CH3 and/or CH4 domains and a hinge region that are derived from different antibody isotypes, i.e., a hybrid Fc portion. For example, in one embodiment, the Fc portion contains CH2 and/or CH3 domains derived from IgG2 or IgG4 and a mutant hinge region derived from IgG1. As used in this application, Fcγ2(h) refers to an embodiment wherein the hinge is derived from IgG1 and the remaining constant domains are from IgG2. Alternatively, a mutant hinge region from another IgG subclass is used in a hybrid Fc portion. For example, a mutant form of the IgG4 hinge that allows efficient disulfide bonding between the two heavy chains can be used. A mutant hinge can also be derived from an IgG2 hinge in which the first two cysteines are each mutated to another amino acid. Such hybrid Fc portions facilitate high-level expression and improve the correct assembly of the Fc-IL-7 fusion proteins. Assembly of such hybrid Fc portions is known in the art and has been described in U.S. Published Patent Application No. 2003-0044423.

In some embodiments, the Fc portion contains amino acid modifications that generally extend the serum half-life of an Fc fusion protein. Such amino acid modifications include mutations substantially decreasing or eliminating Fc receptor binding or complement fixing activity. For example, the glycosylation site within the Fc portion of an immunoglobulin heavy chain can be removed. In IgG1, the glycosylation site is Asn297 within the amino acid sequence Gln-Tyr-Asn-Ser (SEQ ID NO:30). In other immunoglobulin isotypes, the glycosylation site corresponds to Asn297 of IgG1. For example, in IgG2 and IgG4, the glycosylation site is the asparagine within the amino acid sequence Gln-Phe-Asn-Ser (SEQ ID NO:29). Accordingly, a mutation of Asn297 of IgG1 removes the glycosylation site in an Fc portion derived from IgG1. In one embodiment, Asn297 is replaced with Gln. In other embodiments, the tyrosine within the amino acid sequence Gln-Tyr-Asn-Ser (SEQ ID NO:30) is further mutated to eliminate a potential non-self T-cell epitope resulting from asparagine mutation. As used herein, a T-cell epitope is a polypeptide sequence in a protein that interacts with or binds an MHC class II molecule. For example, the amino acid sequence Gln-Tyr-Asn-Ser (SEQ ID NO:30) within an IgG1 heavy chain can be replaced with a Gln-Ala-Gln-Ser (SEQ ID NO:28) amino acid sequence. Similarly, in IgG2 or IgG4, a mutation of asparagine within the amino acid sequence Gln-Phe-Asn-Ser (SEQ ID NO:29) removes the glycosylation site in an Fc portion derived from IgG2 or IgG4 heavy chain. In one embodiment, the asparagine is replaced with a glutamine. In other embodiments, the phenylalanine within the amino acid sequence Gln-Phe-Asn-Ser (SEQ ID NO:29) is further mutated to eliminate a potential non-self T-cell epitope resulting from asparagine mutation. For example, the amino acid sequence Gln-Phe-Asn-Ser (SEQ ID NO:29) within an IgG2 or IgG4 heavy chain can be replaced with a Gln-Ala-Gln-Ser (SEQ ID NO:28) amino acid sequence.

It has also been observed that alteration of amino acids near the junction of the Fc portion and the non-Fc portion can dramatically increase the serum half-life of the Fc fusion protein. (U.S. Published Patent Application No. 2002-0147311). Accordingly, the junction region of an Fc-IL-7 or IL-7-Fc fusion protein of the present invention can contain alterations that, relative to the naturally-occurring sequences of an immunoglobulin heavy chain and IL-7, preferably lie within about 10 amino acids of the junction point. These amino acid changes can cause an increase in hydrophobicity by, for example, changing the C-terminal lysine of the Fc portion to a hydrophobic amino acid such as alanine or leucine. In yet another embodiment of the invention, the C-terminal lysine and preceding glycine of the Fc portion is deleted.

In other embodiments, the Fc portion contains amino acid alterations of the Leu-Ser-Leu-Ser segment near the C-terminus of the Fc portion of an immunoglobulin heavy chain. The amino acid substitutions of the Leu-Ser-Leu-Ser (SEQ ID NO:27) segment eliminate potential junctional T-cell epitopes. In one embodiment, the Leu-Ser-Leu-Ser (SEQ ID NO:27) amino acid sequence near the C-terminus of the Fc portion is replaced with an Ala-Thr-Ala-Thr (SEQ ID NO:26) amino acid sequence. In other embodiments, the amino acids within the Leu-Ser-Leu-Ser (SEQ ID NO:27) segment are replaced with other amino acids such as glycine or proline. Detailed methods of generating amino acid substitutions of the Leu-Ser-Leu-Ser (SEQ ID NO:27) segment near the C-terminus of an IgG1, IgG2, IgG3, IgG4, or other immunoglobulin class molecules, as well as other exemplary modifications for altering junctional T-cell epitopes, have been described in U.S. Published Patent Application No. 2003-0166877.

Spacer

In one embodiment, a spacer or linker peptide is inserted between the carrier protein and the IL-7 fusion protein. For example, the spacer is placed immediately C-terminal to the last amino acid of an Ig constant region. The spacer or linker peptide is preferably non-charged and more preferably non-polar or hydrophobic. The length of a spacer or linker peptide is preferably between 1 and about 100 amino acids, more preferably between 1 and about 50 amino acids, or between 1 and about 25 amino acids, and even more preferably between 1 and about 15 amino acids, and even more preferably less than 10 amino acids. In one embodiment, the spacer contains a sequence $(G_4S)_n$, where n is less than 5. In a preferred embodiment, the spacer contains the sequence $G_4SG_4$ (SEQ ID NO:25). In yet another embodiment, the spacer contains a motif that is recognized as an N-linked glycosylation site. In yet another embodiment, the spacer contains a motif that is recognized by a site specific cleavage agent. In an alternative embodiment of the invention, the carrier protein and IL-7 fusion protein are separated by a synthetic spacer, for example a PNA spacer, that is preferably non-charged, and more preferably non-polar or hydrophobic.

Production of IL-7 Fusion Proteins

Non-limiting methods for synthesizing useful embodiments of the invention are described in the Examples herein, as well as assays useful for testing the in vitro properties, and pharmacokinetic and in vivo activities in animal models.

The IL-7 fusion proteins of the invention can be produced using recombinant expression vectors known in the art. The term "expression vector" refers to a replicable DNA construct used to express DNA which encodes the desired IL-7 fusion protein and which includes a transcriptional unit comprising an assembly of (1) genetic element(s) having a regulatory role in gene expression, for example, promoters, operators, or enhancers, operatively linked to (2) a DNA sequence encoding the desired IL-7 fusion protein which is transcribed into mRNA and translated into protein, and (3) appropriate transcription and translation initiation and termination sequences. The choice of promoter and other regulatory elements generally varies according to the intended host cell. A preferred expression vector of the invention is an Fc expression vector derived from the PdCs-huFc expression vector described in Lo et al., *Protein Engineering* (1998) 11:495.

In a preferred example, the nucleic acid encoding the IL-7 fusion protein is transfected into a host cell using recombinant DNA techniques. In the context of the present invention, the foreign DNA includes a sequence encoding the inventive proteins. Suitable host cells include prokaryotic, yeast or higher eukaryotic cells. Preferred host cells are eukaryotic cells.

The recombinant IL-7 fusion proteins can be expressed in yeast hosts, preferably from *Saccharomyces* species, such as *S. cerevisiae*. Yeast of other genera such as *Pichia* or *Kluyveromyces* may also be employed. Yeast vectors will generally contain an origin of replication from a yeast plasmid or an autonomously replicating sequence (ARS), a promoter, DNA encoding the IL-7 fusion protein, sequences for polyadenylation and transcription termination and a selection gene. Suitable promoter sequences in yeast vectors include the promoters for metallothionein, 3-phosphoglycerate kinase or other glycolytic enzymes, such as enolase, glyceraldehyde-3-phosphate dehydrogenase, hexokinase, pyruvate decarboxylase, phosphofructokinase, glucose-4-phosphate isomerase, 3-phosphoglycerate mutase, pyruvate kinase, triosephosphate isomerase, phosphoglucose isomerase and glucokinase.

Various mammalian or insect cell culture systems can be employed to express recombinant protein. Baculovirus systems for production of proteins in insect cells are well known in the art. Examples of suitable mammalian host cell lines include NS/0 cells, L cells, C127, 3T3, Chinese hamster ovary (CHO), HeLa, and BHK cell lines. Additional suitable mammalian host cells include CV-1 cells (ATCC CCL70) and COS-7 cells both derived from monkey kidney. Another suitable monkey kidney cell line, CV-1/EBNA, was derived by transfection of the CV-1 cell line with a gene encoding Epstein-Barr virus nuclear antigen-1 (EBNA-1) and with a vector containing CMV regulatory sequences (McMahan et al., (1991) *EMBO J.* 10:2821). The EBNA-1 gene allows for episomal replication of expression vectors, such as HAV-EO or pDC406, that contain the EBV origin of replication.

Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences. Commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence.

For secretion of the IL-7 fusion protein from the host cell, the expression vector comprises DNA encoding a signal or leader peptide. In the present invention, DNA encoding the native signal sequence of IL-7 can be used, or alternatively, a DNA encoding a heterologous signal sequence may be used, such as the signal sequence from another interleukin or from a secreted Ig molecule.

The present invention also provides a process for preparing the recombinant proteins of the present invention including culturing a host cell transformed with an expression vector comprising a DNA sequence that encodes the IL-7 fusion protein under conditions that promote expression. The desired protein is then purified from culture media or cell extracts. For example, supernatants from expression systems that secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix, as known in the art. For example, Fc-IL-7 fusion proteins are conveniently captured using a matrix coupled to Protein A.

An "isolated" or "purified" IL-7 fusion protein or biologically active portion thereof is substantially free of cellular material or other contaminating proteins from the cell or tissue source from which the IL-7 fusion protein is derived, or substantially free from chemical precursors or other chemicals when chemically synthesized. The language "substantially free of cellular material" includes preparations of IL-7 fusion protein in which the protein is separated from cellular components of the cells from which it is isolated or recombinantly produced. In one embodiment, the language "substantially free of cellular material" includes preparations of IL-7 fusion protein having less than about 30% (by dry weight) of non-IL-7 fusion protein (also referred to herein as a "contaminating protein"), more preferably less than about 20% of non-IL-7 fusion protein, still more preferably less than about 10% of non-IL-7 fusion protein, and most preferably less than about 5% non-IL-7 fusion protein. When the IL-7 fusion protein or biologically active portion thereof is purified from a recombinant source, it is also preferably substantially free of culture medium, i.e., culture medium represents less than about 20%, more preferably less than about 10%, and most preferably less than about 5% of the volume of the protein preparation.

The term "substantially pure Ig-IL-7 fusion protein" refers to a preparation in which the Ig-IL-7 fusion protein constitutes at least 60%, 70%, 80%, 90%, 95% or 99% of the proteins in the preparation. In one embodiment, the invention includes substantially pure preparations of Ig-IL-7 fusion proteins having a disulfide bonding pattern between Cys2 and Cys92, Cys34 and Cys129, and Cys47 and Cys141. In another embodiment, the invention features substantially pure preparations of Ig-IL-7 fusion proteins where Asn116 is non-glycosylated but Asn70 and Asn91 are glycosylated.

Methods of Treatment Using Fc-IL-7 Proteins

The IL-7 fusion proteins of the invention are useful in treating immune deficiencies and in accelerating the natural reconstitution of the immune system that occurs, for example, after diseases or treatments that are immunosuppressive in nature. For example, IL-7 fusion proteins can be used to treat infectious pathogens, immune disorders, and to enhance the growth (including proliferation) of specific immune cell types. Moreover, the IL-7 fusion proteins can be used in the treatment of cancers such as bladder cancer, lung cancer, brain cancer, breast cancer, skin cancer, and prostate cancer. In one example, it is useful to treat patients who have undergone one or more cycles of chemotherapy with IL-7 fusion proteins as described above to help their immune cells replenish. Alternatively, IL-7 fusion proteins are useful in adoptive T-cell transplantations. For example, IL-7 fusion proteins may be administered to facilitate the expansion and survival of transplanted T-cells, or to expand isolated T-cell populations ex vivo. Alternatively, it is also useful to administer the IL-7 fusion proteins described above to patients with HIV, the elderly, patients receiving a transplant or other patients with suppressed immune system function.

Administration

The IL-7 fusion proteins of the invention can be incorporated into a pharmaceutical composition suitable for administration. Such compositions typically comprise the IL-7 fusion protein and a pharmaceutically-acceptable carrier. As used herein the language "pharmaceutically-acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Medicaments that contain the IL-7 fusion proteins of the invention can have a concentration of 0.01 to 100% (w/w), though the amount varies according to the dosage form of the medicaments.

Administration dose depends on the body weight of the patients, the seriousness of the disease, and the doctor's opinion. However, it is generally advisable to administer about 0.01 to about 10 mg/kg body weight a day, preferably about 0.02 to about 2 mg/kg, and more preferably about 0.5 mg/kg in case of injection. The dose can be administered once or several times daily according to the seriousness of the disease and the doctor's opinion.

Compositions of the invention are useful when co-administered with one or more other therapeutic agents, for example, a molecule also known to be useful to replenish blood cells. For example, the molecule may be erythropoietin which is known to be used to replenish red blood cells, G-CSF which is used to replenish neutrophils or GM-CSF which is used to replenish granulocytes and macrophages.

EXAMPLE 1

Cloning of Human (hu) Fc-IL-7 and huFc-IL-7 Variants

The nucleic acid encoding the mature form of human IL-7 (i.e. lacking its N-terminal signal sequence) is amplified by Polymerase Chain Reaction (PCR), using forward and reverse primers that incorporated the restriction sites for Sma I and Xho I, respectively. The amplified PCR product is cloned into a pCRII vector (Invitrogen, Carlsbad, Calif.), and its sequence verified. The amino acid sequence of mature IL-7 is shown as SEQ ID NO:1. The Sma I/Xho I digested IL-7 fragment is transferred into a likewise treated pdCs-huFc derived expression vector, resulting in a chimeric sequence between huFc and IL-7, with IL-7 placed in-frame, directly downstream of the sequence encoding a CH3 moiety of Fc (see Lo et al., *Protein Engineering* (1998) 11:495).

A series of expression vectors are derived from the pdCs-huFc vector which encodes an Fc fragment that generally includes a hinge, a CH2 domain, and a CH3 domain of Ig, and which have been engineered to incorporate specific alterations in the Fc region. Thus, by shuttling the IL-7 fragment between these vectors, a series of huFc-IL-7 fusion proteins were generated which differ in their Fc backbone. In order to create the various backbones, the appropriate mutations can first be introduced into the Fc sequence by methods known in the art. Since the Fc region of the pdCs-huFc derived vector is flanked by an AflII restriction site and a SmaI restriction site, by subjecting the nucleic acid of the appropriately modified backbone to PCR using primers that incorporate the restriction sites for AflII and SmaI respectively, the resultant Fc encoding nucleic acid fragment can then be substituted into the pdCs-huFc derived vector as an AflII to SmaI fragment. The AflII sequence CTTAAGC (SEQ ID NO:24) is upstream of the Fc sequence beginning GAGCCCAAA (SEQ ID NO:23), which represents the beginning of the hinge region as shown in FIG. 20. The SmaI site CCCGGGT (SEQ ID NO:17) is towards the end of the CH3 region as shown by the underlined nucleic acids in FIG. 12 and encodes the Pro-Gly amino acids proceeding the alanine residue from the lysine to alanine mutation at the end of the CH3 region.

For example, huFcγ1-IL-7 is constructed having the hinge region, the CH2 and the CH3 domains derived from the IgGγ1 subclass. In the context of an Fc fusion protein, the IgGγ1 hinge region in addition contains a mutation substituting the first cysteine for serine. The sequence of the encoded fusion protein is depicted in FIG. 4 (SEQ ID NO:4), while the sequence in SEQ ID NO:22 encodes the mature huFcγ1 backbone of the vector.

In addition, Fcγ1-IL-7 fusion proteins were generated that included the dipeptide mutation YN to AQ to eliminate the glycosylation site on Fc (corresponding to N297 in IgGγ1) as well as a potential immunogenic T-cell epitope, according to the methods described above. The mature Fc backbone sequence for huFcγ1(YN>AQ) is disclosed in SEQ ID NO:21. The substitution of alanine and glycine in place of tyrosine and asparagine was accomplished by first introducing mutations into the Fc backbone by an overlap PCR approach. Two overlapping complementary mutagenic primers were used to generate two PCR fragments, which were used as the template in a second round of amplification to produce a single fragment containing the appropriate codon substitutions. The mutagenic primer in the sense direction was 5'-AGCAGGCCCAGAG CACGTACCGT-GTGGT-3' (mutation underlined) (SEQ ID NO:36). The complementary strand was 5'-GTACGTGCT CTGGGCCTGCTCCTCCCGC-3' (SEQ ID NO:37). The flanking forward primer was 5'-CTCTCTGCAGAGC-CCAAA TCT-3' (SEQ ID NO:38), which also contains a PstI site. In the antisense direction, the flanking reverse primer was 5'CAGGGTGTACACCTGTGGTTC-3' (SEQ ID NO:33), which also contains a BsrGI site. After amplification, the sequence was verified through standard methods and was subject to restriction by BsrGI and PstI. The resultant fragment was then substituted for the non-mutant fragment of the Fc region.

The huFcγ2(h)(FN>AQ)-IL-7 was also constructed using the techniques previously described. This fusion protein includes an altered hinge region which was derived from IgGγ1 subclass, while the CH2 and CH3 domains were derived from IgGγ2 subclass. Additionally, the dipeptide mutation FN to AQ was included to eliminate the glycosylation site on Fc (corresponding to N297 in IgGγ1) as well as a potential immunogenic T-cell epitope. The sequence of the encoded fusion protein is depicted in FIG. 5 (SEQ ID NO:5). The sequence of the mature Fc backbone huFcγ2(h)(FN>AQ) is shown in SEQ ID NO:19).

In addition, Fc-IL-7 fusion proteins were generated which included a flexible linker sequence between the Fc moiety and the IL-7 moiety. For example, a linker polypeptide with the sequence GGGGSGGGGSGGGGS (linker1, SEQ ID NO:34) was inserted. To generate huFcγ1(linker1)-IL-7, a synthetic oligonucleotide duplex of the sequence 5'-G GGT GCA GGG GGC GGG GGC AGC GGG GGC GGA GGA TCC GGC GGG GGC TC-3' (SEQ ID NO:18) was inserted by blunt-end ligation at the unique SmaI site of the expression vector pdCs-huFc-IL-7 and the orientation of the duplex was verified. The forward primer was designed such that the amino acid residues Pro-Gly encoded by the codons spanning the SmaI site (C CCG GGT) (SEQ ID NO:17), and the ensuing Ala residue (resulting from the encoded lysine to alanine substitution) of the CH3 region, were maintained. The amino acid sequence of the encoded fusion protein is shown in FIG. 6 (SEQ ID NO:6).

Additional Fc-IL-7 fusion proteins were constructed that included a shorter linker polypeptide with the sequence GGGGSGGGG (linker2, SEQ ID NO:25). To generate huFcγ1(YN>AQ)(linker2)-IL-7, an amplified PCR product, obtained from the primer pair 5'-CCCGGGCGCCGGCG-GTGGAGGATCAGGTGGTGGCGGTGAT TGTGA TAT-TGAAGGTAAAGATG-3' (containing the encoded linker sequence, SEQ ID NO:15) and 5'-ATCATGTCTGGATC-CCTCGA-3' (SEQ ID NO:14) on an appropriate pdCs-Fc-IL-7 template plasmid, was cloned into a pCRII vector (Invitrogen, Carlsbad, Calif.), and its sequence verified. A Xma I/Xho I digested fragment encoding linker2/IL-7 was then transferred into a likewise treated pdCs-huFc derived expression vector. The vector was modified to contain the mature Fc backbone huFcγ1(YN>AQ) of SEQ ID NO:21. The amino acid sequence of the encoded fusion protein is shown in FIG. 7 (SEQ ID NO:7).

Similarly, huFcγ1(YN>AQ,d)(linker2)-IL-7 was generated, using the primer pair 5'-CCCGGGCGGTGGAGGAT-CAGGTGGTGGCGGTGATTGTGATAT TGAAGG-TAAAGATG-3' (SEQ ID No:16) and 5'-ATCATGTCTGGATCCCTCGA-3' (SEQ ID NO:12). huFcγ1(YN>AQ,d)(linker2)-IL-7 differs from the preceding fusion protein huFcγ1(YN>AQ)(linker2)-IL-7 in that it lacks the terminal two amino acid residues of the Fc portion of the fusion protein. Specifically, rather than terminating in with the sequence . . . ATATPGA (SEQ ID NO:11), the Fc portion ends with the sequence . . . ATATP (SEQ ID NO:10). The amino acid sequence of the encoded fusion protein is shown in FIG. 8 (SEQ ID NO:8).

EXAMPLE 2

Transfection and Expression of Fc-IL-7 Fusion Proteins

Electroporation was used to introduce the DNA encoding the IL-7 fusion proteins described above into a mouse myeloma NS/0 cell line. To perform electroporation NS/0 cells were grown in Dulbecco's modified Eagle's medium supplemented with 10% heat-inactivated fetal bovine serum, 2 mM glutamine and penicillin/streptomycin. About $5\times10^6$ cells were washed once with PBS and resuspended in 0.5 ml PBS. 10 μg of linearized plasmid DNA for huFcγ1-IL-7 was then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 μF. Cells were allowed to recover for 10 min on ice, after which they were resuspended in growth medium and plated onto two 96 well plates.

Stably transfected clones were selected by their growth in the presence of 100 nM methotrexate (MTX), which was added to the growth medium two days post-transfection. The cells were fed every 3 days for two to three more times, and MTX-resistant clones appeared in 2 to 3 weeks. Supernatants from clones were assayed by anti-Fc ELISA to identify clones that produced high amounts of the IL-7 fusion proteins. High producing clones were isolated and propagated in growth medium containing 100 nM MTX. Typically, a serum-free growth medium, such as H-SFM or CD medium (Life Technologies), was used.

EXAMPLE 3

Biochemical Analysis of huFc-IL-7 Fusion Proteins

Routine SDS-PAGE characterization was used to assess the integrity of the fusion proteins. Differences between the huFc-IL-7 variants huFcγ1-IL-7, huFcγ2(h)(FN>AQ)-IL-7, huFcγ1 (linker1)-IL-7, huFcγ1(YN>AQ)(linker2)-IL-7 and huFcγ1(YN>AQ,d)-IL-7 were investigated. The huFc-IL-7 fusion proteins, expressed from NS/0 cells, were captured on Protein A Sepharose beads (Repligen, Needham, Mass.) from the tissue culture medium into which they were secreted, and were eluted by boiling in protein sample buffer, with or without a reducing agent such as β-mercaptoethanol. The samples were separated by SDS-PAGE and the protein bands were visualized by Coomassie staining. By SDS-PAGE the tested huFc-IL-7 fusion proteins were generally well expressed, as they were present substantially as a single band on the gel; it was found that in samples of huFc-IL-7 variants that included a linker, secondary bands, which may represent clipped material, were noticeably reduced.

Purified huFc-IL-7 fusion proteins were also analyzed by size exclusion chromatography (SEC) to assess the extent to which the huFc-IL-7 variants were aggregated. Briefly, the cell culture supernatant was loaded onto a pre-equilibrated Fast-Flow Protein A Sepharose column, the column was washed extensively in a physiological buffer (such as 100 mM Sodium Phosphate, 150 mM NaCl at neutral pH), and the bound protein was eluted at about pH 2.5 to 3 in same salt buffer as above. Fractions were immediately neutralized.

It was found that for each of the fusion proteins tested at least 50% of the product was monomeric, and generally more than 65%. "Monomeric," as used herein, refers to non-aggregated proteins. It is understood that proteins with an Fc portion normally form a disulfide-bonded complex which normally include two polypeptide chains (unless the two Fc portions are present within the same polypeptide) and may be thought of as a "unit-dimer". "Monomeric" is not intended to exclude such disulfide-bonded species, but only to connote that the proteins are non-aggregated. To obtain a virtually monomeric huFc-IL-7 fusion protein preparation (around 98%), the eluate from a Sepharose-ProteinA purification was loaded onto a preparative SEC column (Superdex) and the monomeric peak fraction was collected. Typically, the concentration of the recovered protein was around 1 mg/ml. If required, the sample was concentrated, for example by spin dialysis (e.g. VivaSpin) with a molecular weight cut-off of 10-30 kDa.

Disulfide Bonding

IL-7 contains six Cys residues which could make disulfide bonds, at positions Cys2, Cys34, Cys47, Cys92, Cys129 and Cys141 of the mature IL-7 protein sequence. The folding of huFcγ1-IL-7 was assessed by determining the pattern of disulfide bonds present in the IL-7 moiety of the fusion protein. Briefly, peptide maps of huFcγ1-IL-7 were generated from trypsinized material and analyzed for the presence of signature peptide fragments. huFcγ1-IL-7 protein was trypsinized either in a native form or after reduction and alkylation. To account for peptide fragments that may be glycosylated, samples of the native and denatured proteins were additionally treated with PNGaseF to remove glycosyl chains prior to tryptic digestion. Peptide fragments were fractionated by HPLC, and their mass was determined by mass spectroscopy.

In the context of Fcγ1-IL-7, a peptide fragment containing the disulfide bond Cys47-Cys141 ("3-6") would be predicted to have a mass of 1447.6, whereas a peptide fragment containing the disulfide bond Cys2-Cys141 ("1-6") would be predicted to have a mass of 1426.6. Similarly, a peptide fragment containing the disulfide bond Cys34-Cys129 ("2-5") would be predicted to have a mass of 2738.3. Indeed, peptide fragments of a mass of 1447.6 ("3-6") and of 2738.3 ("2-5") were identified in samples derived from the native Fc-IL-7 protein regardless of whether the samples were treated with PNGaseF or not, but not in samples from reduced Fc-IL-7. Conversely, the peptide fragment of a mass of 1426.6 ("1-6") was not found in any sample. Thus, Fcγ1-IL-7 contained the disulfide bonds Cys47-Cys141 and Cys34-Cys129, but not Cys2-Cys141. It was noted that a peptide fragment of the predicted mass of 2439.2, corresponding to a fragment containing Cys2-Cys92 ("1-4") was identified only in the sample from the native fusion protein treated with PNGaseF. In fact, Cys92 lies within the tripeptide motif Asn91Cys92Thr93, indicating that Asn91 was glycosylated in huFcγ1-IL-7. Thus, in huFcγ1-IL-7 the disulfide bonding pattern was consistent with Cys2-Cys92, Cys34-Cys129, and Cys47-Cys141. This experimentally determined configuration of disulfide bonds of Fc-IL-7 stands in contrast to the experimentally determined configuration reported for bacterially produced and re-folded IL-7 (Cosenza et al. (1997) *JBC* 272:32995).

N-Linked Glycosylation Sites

Human IL-7 contains three potential glycosylation sites, at positions Asn70, Asn91 and Asn116 of the mature IL-7 protein sequence. Peptide maps of huFcγ1-IL-7 (reduced/alkylated) were analyzed for the presence of signature peptide fragments. If glycosylated, these signature fragments would only be revealed in samples treated with PNGaseF. Masses of 1489.7, 1719.9 and 718.3 would be predicted for tryptic peptide fragments containing the unmodified residues for Asn70, Asn91, and Asn116, respectively.

Indeed, peptide fragments of a mass of 1489.7 and of 1719.9 were identified in samples that had been treated with PNGaseF, but were absent in the untreated sample, indicating that Asn70 (contained in the sequence . . . MNSTG . . . ) (SEQ ID NO:31), and Asn91 (contained in the sequence . . . LNCTG . . . ) (SEQ ID NO:32), were indeed glycosylated. Surprisingly, a tryptic fragment of a mass of 718.3, corresponding to SLEENK (SEQ ID NO:35), was identified in both the PNGaseF treated sample and the untreated sample, indicating that Asn116 was not glycosylated. This was not expected because Asn116 in the human IL-7 sequence . . . PTKSLEENKSLKE . . . (SEQ ID NO:13) (see SEQ ID NO:1) is predicted to be an N-linked glycosylation site. The NKS putative glycosylation site is conserved in sheep and cows as well as humans.

The analysis of disulfide bonding patterns and N-linked glycosylation sites, repeated with samples of Fcγ1-(linker1)-IL-7 and of Fcγ2h(FN>AQ)-IL-7, gives similar results.

EXAMPLE 4

ELISA Procedures

The concentrations of protein products in the supernatants of MTX-resistant clones and other test samples was determined by anti-huFc ELISA, as described in detail below. ELISA plates were coated with AffiniPure Goat anti-Human IgG (H+L) (Jackson Immuno Research Laboratories, West Grove, Pa.) at 5 µg/mL in PBS, and 100 µL/well in 96-well plates. Coated plates were covered and incubated at 4° C. overnight. Plates were washed 4 times with 0.05% Tween (Tween 20) in PBS, and blocked with 1% BSA/1% goat serum in PBS, 200 µL/well. After incubation with the blocking buffer at 37° C. for 2 hrs, the plates were washed 4 times with 0.05% Tween in PBS and tapped dry. Test samples were diluted as appropriate in sample buffer (1% BSA/1% goat serum/0.05% Tween in PBS). A standard curve was prepared using a chimeric antibody (with a human Fc) of known concentration. To prepare a standard curve, serial dilutions were made in the sample buffer to give a standard curve ranging from 125 ng/mL to 3.9 ng/mL. The diluted samples and standards were added to the plate, 100 µL/well and the plate incubated at 37° C. for 2 hr. After incubation, the plate was washed 8 times with 0.05% Tween in PBS. To each well 100 µL of the secondary antibody horseradish peroxidase-conjugated anti-human IgG was added, diluted to around 1:120,000 in sample buffer. The exact dilution of the secondary antibody was determined for each lot of the HRP-conjugated anti-human IgG. After incubation at 37° C. for 2 hr, the plate was washed 8 times with 0.05% Tween in PBS.

The substrate solution was added to the plate at 100 µL/well. This solution was prepared by dissolving 30 mg of OPD (o-phenylenediamine dihydrochloride (OPD), (1 tablet) into 15 mL of 0.025 M citric acid/0.05 M $Na_2HPO_4$ buffer, pH 5, which contained 0.03% of freshly added hydrogen peroxide. The color was allowed to develop for about 30 minutes at room temperature in the dark. The reaction was stopped by adding 4N sulfuric acid, 100 μL/well. The plate was read by a plate reader, which was set at both 490 and 650 nm and programmed to subtract the background OD at 650 nm from the OD at 490 nm.

The concentration of human IL-7 in serum samples of animals treated with huFc-IL-7 fusion proteins or recombinant human IL-7 was determined by ELISA, essentially as described above. Human IL-7 was captured via a mouse anti-human IL-7 antibody (R&D Systems, Minneapolis, Minn.) and detected with a goat anti-human IL-7 biotin antibody (R&D Systems, Minneapolis, Minn.).

EXAMPLE 5

Purification of huFc-IL-7 Proteins

A standard purification of Fc-containing fusion proteins was performed based on the affinity of the Fc protein moiety for Protein A. Briefly, NS/0 cells expressing the appropriate fusion protein, were grown in tissue culture medium and the supernatant containing the expressed protein was collected and loaded onto a pre-equilibrated Past Flow Protein A Sepharose column. The column was then washed extensively with buffer (such as 100 mM Sodium Phosphate, 150 mM NaCl at neutral pH). Bound protein was eluted at a low pH (pH 2.5-3) in same buffer as above and fractions were immediately neutralized.

To obtain a non-aggregated huFc-IL-7 fusion protein preparation (around 98% monomer), the eluate was loaded onto a preparative SEC column (Superdex) and the monomeric peak fraction was collected. Typically, the concentration of the recovered protein was around 0.5 mg/ml to 2 mg/ml, and where appropriate the sample was concentrated by spin dialysis (e.g. Viva Spin with a molecular weight cut-off of 30 kDa).

EXAMPLE 6

In Vitro Activity of huFc-IL-7 Proteins

The cytokine activity of the purified huFc-IL-7 fusion proteins was determined in vitro in a cellular proliferation bioassay. Human PBMC (Peripheral Blood Mononuclear Cells) were activated by PHA-P to produce cells which were responsive to IL-7. Proliferation was measured in a standard thymidine incorporation assay. Briefly, PBMC's were first incubated for five days with 10 microgram/ml PHA-P, cells were washed and then incubated in a medium supplemented with the huFc-IL-7 fusion proteins, in a dilution series, for a total of 48 hours. During the final 12 hours, the samples were pulsed with 0.3 μCi of [methyl-3H]thymidine (Dupont-NEN-027). Cells were then washed extensively, harvested and lysed onto glass filters. 3H-thymidine incorporated into DNA was measured in a scintillation counter. As a standard, wild type huIL-7 protein, obtained from R&D Systems (Minneapolis, Minn.), or obtained from the National Institute for Biological Standards and Control (NIBSC), was assayed.

An ED50 value of cell proliferation for huFc-IL-7 fusion proteins was obtained from plotting a dose response curve according to standard techniques, and determining the protein concentration that resulted in half-maximal response. The fusion proteins huFcγ1-IL-7, huFcγ2(h)(FN>AQ)-IL-7, and huFcγ1(linker1)-IL-7 were evaluated. The ED50 values of the fusion proteins were fairly similar to one another, falling within a 3-fold range from one another. Therefore, it was found that these alterations in the Fc moiety have little influence on IL-7 activity of the fusion protein.

In addition, it was found that the ED50 values of these fusion proteins were about 3- to 10-fold higher than the ED50 value obtained for huIL-7 commercially available from R&D Systems. Since this commercial preparation is produced in bacteria and is not glycosylated, enzymatically deglycosylated huFcγ1-IL-7 protein, by treatment with PNGaseF, was evaluated. It was found to have similar activity to the untreated form. Without wishing to be bound by theory, the somewhat decreased activity of the fusion proteins may have been due not to glycosylation of the IL-7 moiety but instead to a steric effect resulting from a constrained N-terminus of the IL-7 moiety.

EXAMPLE 7

Pharmacokinetics of huFc-IL-7 Proteins

The pharmacokinetic (PK) profiles of an huFc-IL-7 fusion protein and of recombinant human IL-7 (Peprotech, Rocky Hill, N.J.) were evaluated, and the results are depicted in FIG. 13. A single subcutaneous injection of equimolar amounts of huFcγ2(h)(FN>AQ)-IL-7 or of recombinant human IL-7 (50 micrograms) was administered to groups of C57BL6/J mice. Blood samples were obtained by retro-orbital bleeding at injection (i.e., at t=0 min), and at 30 min, 1 hr, 2 hrs, 4 hrs, 8 hrs, 24, 48, 72, 96, 120 and 144 hrs post-injection. Samples were collected in heparin-tubes to prevent clotting, and cells were removed by centrifugation in a high-speed Eppendorf microcentrifuge for 4 min at 12,500 g. PK values were calculated with the PK solutions 2.0™ software package (Summit Research Services, Montrose, Colo.).

The concentration of administered IL-7 was determined in quadruplicate plasma samples at each time point by an ELISA specific for human IL-7. It was found that the pharmacokinetic behavior of the huFc-IL-7 and recombinant IL-7 differed dramatically. For recombinant human IL-7, the maximum concentration ($C_{max}$) was 23.5 ng/ml at 2.0 hours post injection ($T_{max}$), whereas for huFc-IL-7 $C_{max}$ was 1588.7 ng/ml 24 hours post injection. In addition, while recombinant human IL-7 was absorbed more rapidly than huFc-IL-7 (α-phase half-life 0.9 hours vs. 12.4 hours), huFc-IL-7 was eliminated approximately 9-fold more slowly from circulation during the β-phase. Thus, in terms of AUC (area under the curve) as a measure of total drug exposure, mice receiving huFc-IL-7 had a 572-fold higher exposure to the administered protein than mice receiving recombinant human IL-7. These data demonstrate a significant improvement of huFc-IL-7 fusion proteins relative to free recombinant human IL-7 with regards to their PK. It was further found that the PK profiles of huFc-IL-7 fusion proteins, such as huFcγ1-IL-7 and huFcγ2(h)(FN>AQ)-IL-7, huFcγ1(YN>AQ)(linker2)-IL-7, and huFcγ1(YN>AQ,d)(linker2)-IL-7, which were administered to the mice by intravenous injection, were similar to one another.

EXAMPLE 8

Efficacy of huFc-IL-7 in Lymphopenic Mice After Bone Marrow (BM) Transplantation The efficacy of huFc-IL-7 fusion proteins compared to recombinant human IL-7 was evaluated in vivo. For example, huFcγ2(h)(FN>AQ)-IL-7 or recombinant human IL-7 (Peprotech, Rocky Hill, N.J.) was administered to lymphopenic mice after transplantation of T-cell-depleted bone marrow (BM), and the recovery of immune cell populations was assessed.

Essentially, recipient mice were lethally irradiated prior to BM transplantation with two doses of 600 cGy total body irradiation at a 4 hr interval, and BM cells re-suspended in PBS were infused into tail veins of recipient mice. At regular intervals from Day 5 onwards, an equimolar amount of huFc-IL-7 (7 μg) or recombinant human IL-7 (2.5 μg) (Peprotech, Rocky Hill, N.J.) was administered subcutaneously to the recipient mice. Over the course of the experiment, recipient mouse blood samples were taken, and lymphocyte cell concentrations in the samples were measured.

For BM cell transplantations, BM cells were obtained aseptically from femurs and tibias of BL/6.SJL ($H2^b$, CD45.1) mice (Jackson Labs, Bar Harbor, Me.) and depleted of T-cells by removing magnetically labeled T-cells over MACS® columns (Miltenyi Biotec, Auburn, Calif.). The degree of T-cell depletion was monitored by FACS analysis with fluorescently labeled antibodies against CD45, αβ-TCR (T-cells) and 7-Amino Actinomycin D (7-AAD, apoptotic cells) (Calbiochem, X). $10\times10^6$ live (7-AAD-negative) BM cells (containing less than 1% T-cells) were used per recipient mouse. In congeneic BM transplantations, B6 ($H2^b$, CD45.2) mice were used as the recipient mouse strain, and in allogeneic BM transplantations B6C3F1 ($H2^{b/k}$, CD45.2) mice were chosen.

Lymphocyte cell concentrations (as presented in Table 1) were measured essentially as described by Brocklebank and Sparrow (Brocklebank and Sparrow (2001) *Cytometry* 46:254). Briefly, fluorescent beads (TruCOUNT™ Tubes, BD Biosciences, San Jose, Calif.) were dissolved in 40 μl of PBS containing a mixture of lymphocyte-specific antibodies. Subsequently, 10 μl of anti-coagulated blood was added, mixed and incubated for 30 minutes in the dark at room temperature. Red blood cells were lysed in 450 μl of Red Blood Cell lysis solution (BD Biosciences, San Jose, Calif.) and samples were analyzed by flow cytometry (BD FACS-Calibur™, BD Biosciences, San Jose, Calif.). The concentration of a particular lymphocyte population (e.g. B-cells, T-cells or total leukocytes) was determined by creating separate gates around lymphocytes and fluorescent beads and reading the number of events within each gate. The number of gated lymphocytes per microliter was calculated by dividing the number of events in a gated lymphocyte region by the number of events in the gated bead region. This number was multiplied by the fraction of the number of beads per TruCOUNT™ tube (provided by the supplier) over the sample volume and finally multiplied by the sample dilution factor.

Figure 16:
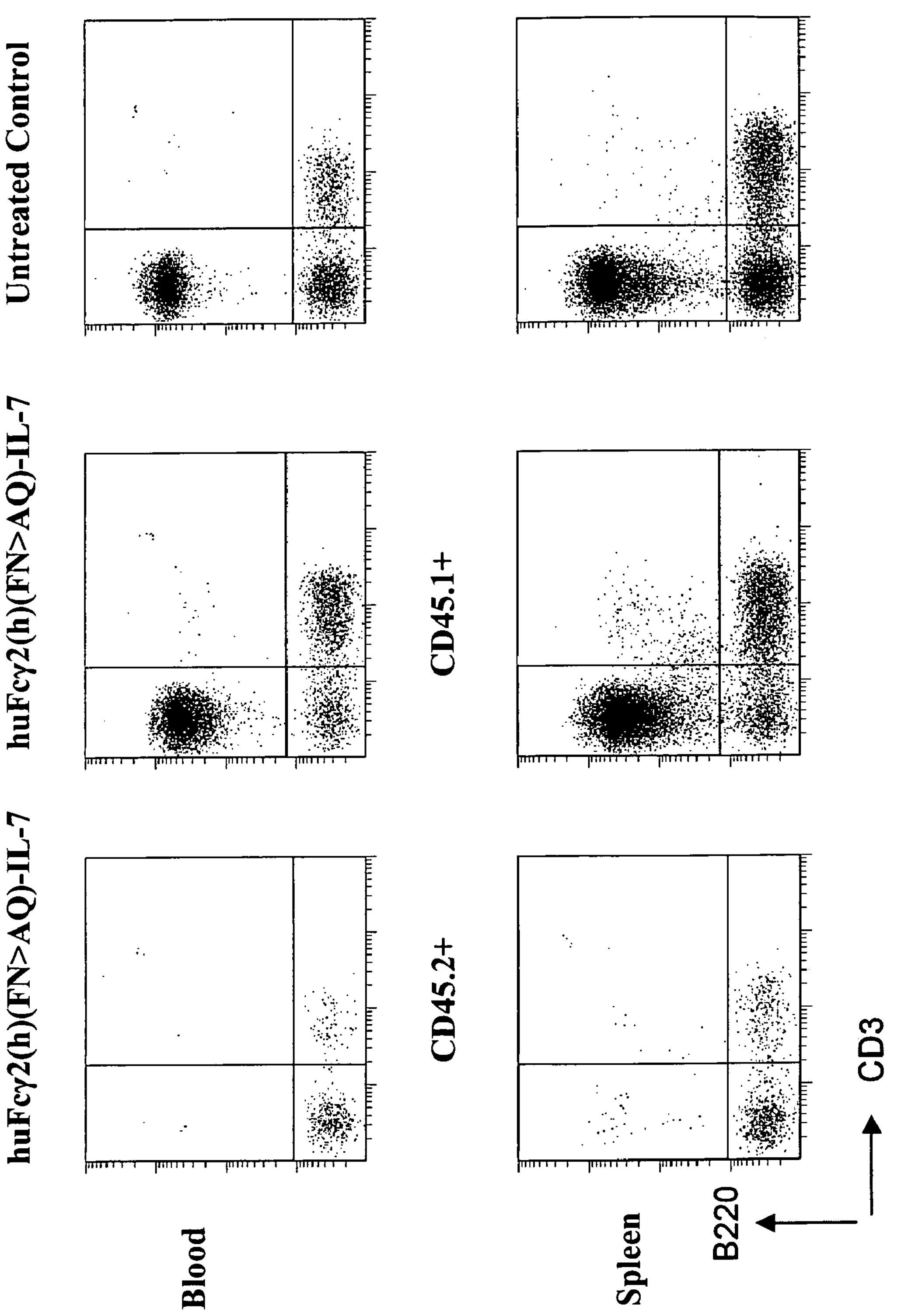
FIG. 16 is a dot plot representing lymphocyte populations of samples from the blood (top row) and spleen (bottom row) of irradiated, bone marrow transplanted mice treated with huFcγ2(h)(FN>AQ)-IL-7 (first two columns), and untreated controls (last column). The first column represents reconstituted endogenous lymphocytes (CD45.2+), and the second column represents reconstituted donor lymphocytes (CD45.1+). T-Lymphocytes were detected as CD3 positive cells shown in the lower right quadrant. B-lymphocytes were detected as B220 positive cells, shown in the upper left quadrant.

In one experiment, lymphocyte reconstitution was assessed in a congeneic BM transplantation setting, using materials and methods specified above. Recipient mice were injected with huFcγ2(h)(FN>AQ)-IL-7 at a dose of 7 μg (125 μg IL-7/kg body weight), and lymphocyte cells were measured as described. Donor lymphocytes were detected as CD45.1 positive cells, whereas endogenous lymphocytes of the recipient mice were detected as CD45.2 positive cells. Lymphocyte B-cells and T-cells were identified using B220 and CD3 lymphocyte markers respectively. It was found that by Day 49, donor lymphocytes (CD45.1 positive cells) had repopulated the recipient mice to levels comparable to non-irradiated control mice, while endogenous lymphocytes (CD45.2 positive cells) had not significantly expanded. In addition, the treatment with the huFc-IL-7 fusion protein did not cause significant toxicity. These results demonstrated the efficacy of the fusion protein in expanding adoptively transferred lymphocyte populations. These results are depicted in FIG. 16.

In another experiment, an allogeneic BM transplantation model, which may better simulate a clinical transplantation setting, was used to compare a huFc-IL-7 fusion protein to recombinant human IL-7, and the results are shown in Table 1. Again, methods and materials described above were used. huFcγ2(h)(FN>AQ)-IL-7 and human IL-7 (equivalent of 125 μg IL-7/kg body weight) were administered either every other day (q2d) or once a week (q7d) from Day 5 to Day 56 after transplantation. PBS-treated donor mice and irradiated, bone marrow recipient mice treated with PBS served as controls.

Figure 14:
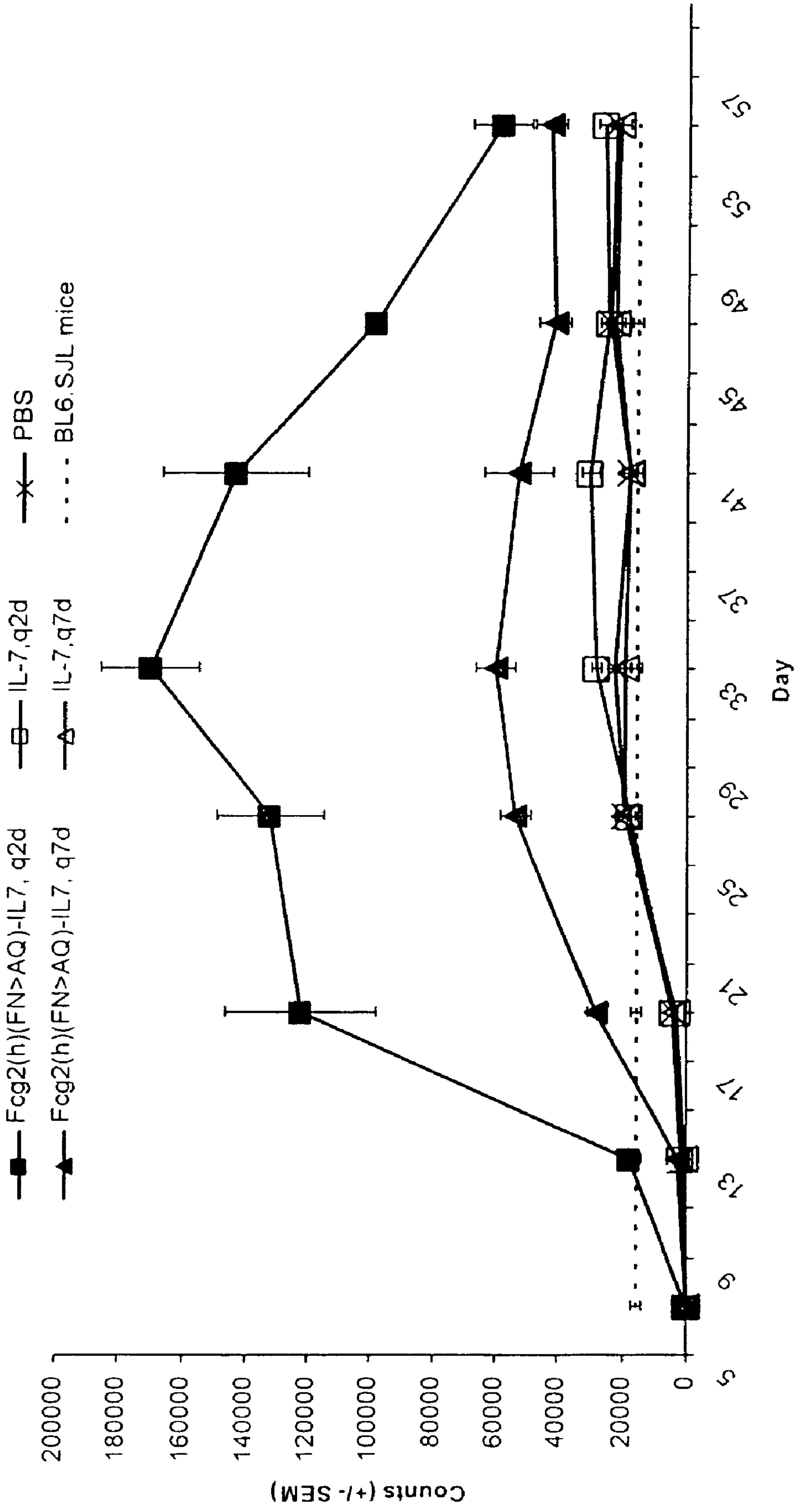
FIG. 14 is a graphical representation of B-cell reconstitution in irradiated, bone marrow transplanted mice treated with recombinant human IL-7 (open symbols), human Fc-IL-7 (filled symbols) or PBS (X). Proteins were administered every other day (squares) or once a week (triangles). The stippled line represents B-cell concentration in donor mice.

In recipient mice treated with the fusion protein, donor-derived B-cells ($CD45.1^+$, $B220^+$, $CD19^+$) reached baseline levels (as defined by the blood concentration of B-cells in donor control mice) 14 or 16 days after transplantation, when given q2d or q7d, respectively. In contrast, in recipient mice treated with recombinant human IL-7, neither dosing regimen had an effect; B-cell numbers in PBS-treated and human IL-7-treated recipient mice required about the same time to reach baseline levels, about 28 days. In addition to accelerated B-cell reconstitution, huFc-IL-7 treatment promoted the continuous expansion of B-cells until Day 33: huFc-IL-7 administered q2d resulted in a 7-fold increase, whereas administered q7d resulted in a 2.5-fold increase in B-cell numbers compared to control mice. After Day 33, B-cell numbers declined, but were still approximately 2-fold higher than in control mice. Also, after Day 33, levels of administered IL-7 proteins declined in the blood, which partially may be due to the formation of neutralizing antibodies to the human fusion protein. FIG. 14 represents these results of B-cell reconstitution in irradiated, bone marrow transplanted mice treated with recombinant human IL-7 and huFC-IL-7.

Figure 15:
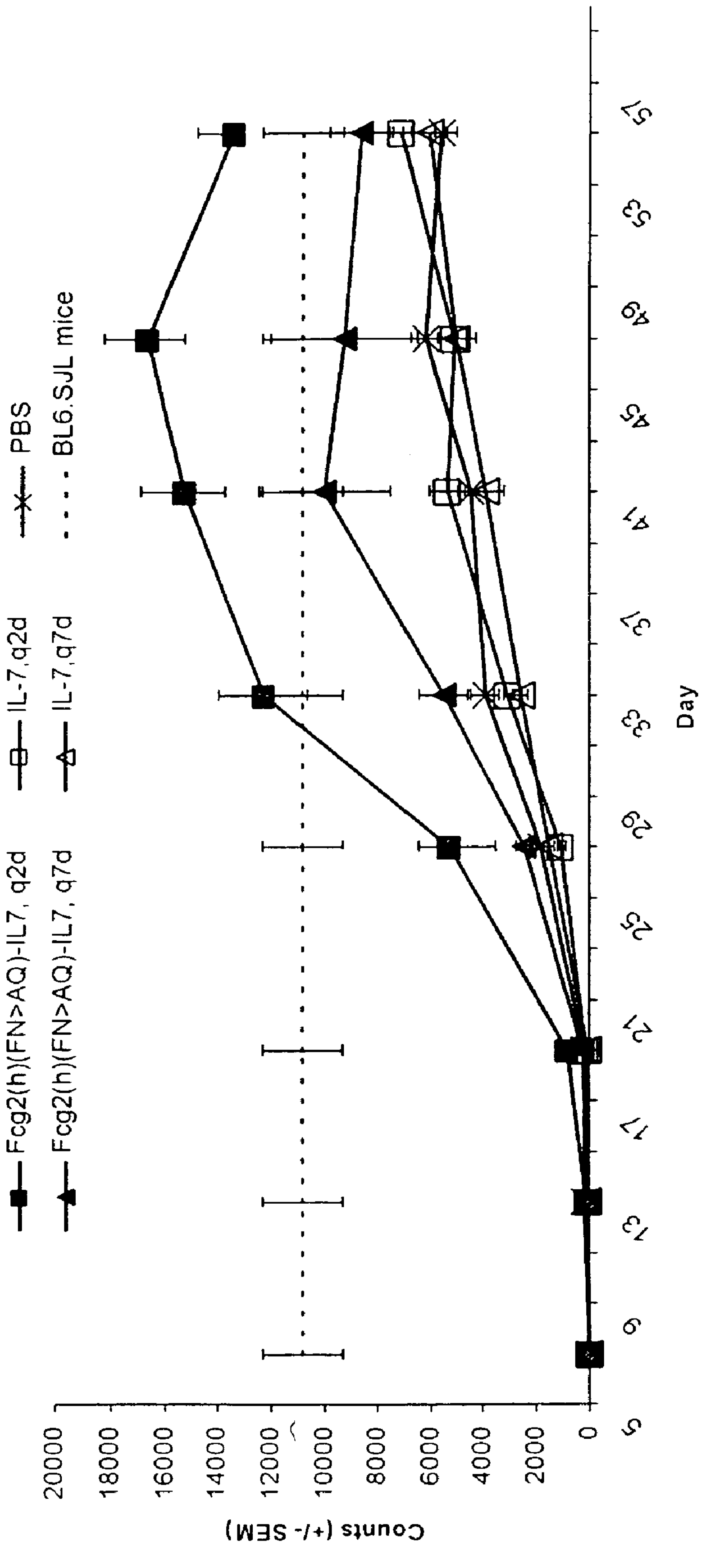
FIG. 15 is a graphical representation of T-cell reconstitution in irradiated, bone marrow transplanted mice treated with recombinant human IL-7 (open symbols), human Fc-IL-7 (filled symbols) or PBS (X). Proteins were administered every other day (squares) or once a week (triangles). The stippled line represents T-cell concentration in donor mice.

A similar result was observed regarding donor-derived T-cells ($CD45.1^+$, $CD3^+$, $TCR\alpha\beta^+$). Treatment with the huFc-IL-7 fusion protein resulted in accelerated T-cell reconstitution, whereas treatment with recombinant human IL-7 did not. Maximum T-cell levels were reached around Day 49. However, T-cell numbers above baseline (i.e., blood concentration of T-cells in donor mice) were only achieved with a q2d dosing schedule of the huFc-IL-7 fusion protein, reaching about 1.5 fold the number of T-cells in the control mice. FIG. 15 represents these results of T-cell reconstitution in irradiated bone marrow transplanted mice treated with recombinant human IL-7 and huFc-IL-7.

Despite the transiently high numbers of donor B-cells and T-cells in the recipient mice under certain conditions, none of the experimental mice showed any signs of morbidity during the course of the experiment. Analysis of internal organs at Day 55 did not reveal pathological abnormalities in liver, kidney, lung, spleen, thymus, lymph nodes, stomach, small intestine and colon. Thus, this allogeneic transplantation experiment demonstrated that the huFc-IL-7 fusion protein was significantly superior in vivo over recombinant human IL-7 in reconstituting lymphocytes after myeloablative conditioning.

TABLE 1

Effect of huFc-IL-7 fusion protein on immune cell reconstitution.

| | Treatment | | Number of cells per microliter of blood Day 7 | 13 | 19 | 27 | 33 | 41 | 47 | 55 |
|---|---|---|---|---|---|---|---|---|---|---|
| I. Donor Derived Leukocytes (CD45.1$^+$) | | | | | | | | | | |
| a.) Allogeneic BMT into B6C3 mice | PBS | AVG | 580.8 | 3576.8 | 4384.0 | 16805.6 | 20732.8 | 16395.2 | 21462.4 | 20329.6 |
| | | SEM | 324.5 | 1717.0 | 1474.2 | 8367.6 | 10065.3 | 7997.3 | 11230.2 | 9693.2 |
| | huFc-IL-7, q2d | AVG | 248.8 | 26597.0 | 130253.6 | 148048.0 | 194266.4 | 168794.0 | 127848.0 | 79175.2 |
| | | SEM | 89.3 | 4786.2 | 25106.8 | 18786.3 | 17131.1 | 25949.9 | 981.0 | 10740.2 |
| | huFc-IL-7, q7d | AVG | 278.4 | 5848.8 | 32308.0 | 64256.0 | 74103.2 | 69042.4 | 55989.6 | 58519.2 |
| | | SEM | 106.3 | 762.9 | 2786.3 | 6081.4 | 8345.9 | 14497.4 | 5989.8 | 6583.8 |
| | human IL-7, q7d | AVG | 270.7 | 6020.0 | 6922.7 | 24278.7 | 37353.3 | 42166.7 | 33570.7 | 38138.7 |
| | | SEM | 84.9 | 1229.2 | 1089.7 | 5235.3 | 2697.0 | 4691.4 | 764.5 | 3273.6 |
| | human IL-7, q7d | AVG | 229.0 | 4603.0 | 4963.0 | 27443.0 | 27027.0 | 27797.0 | 32675.0 | 33205.0 |
| | | SEM | 31.9 | 435.6 | 654.1 | 2513.8 | 1813.4 | 4084.6 | 6307.8 | 4894.7 |
| b.) B6.SJL Control mice | PBS | AVG | 30744.5 | | | | | | | |
| | | SEM | 3018.6 | | | | | | | |
| II. Donor Derived B-cells (CD45.1$^+$CD19$^+$B220$^+$) | | | | | | | | | | |
| a.) Allogeneic BMT into B6C3 mice | PBS | AVG | 32.0 | 1013.3 | 4257.3 | 19294.7 | 22549.3 | 17842.7 | 23841.3 | 22296.0 |
| | | SEM | 5.7 | 25.7 | 661.1 | 2858.5 | 2625.4 | 1691.6 | 3783.7 | 1474.5 |
| | huFc-IL-7, q2d | AVG | 16.0 | 17830.0 | 122122.4 | 131862.4 | 169745.6 | 142972.0 | 98571.0 | 58661.6 |
| | | SEM | 5.7 | 3755.4 | 24028.4 | 16974.5 | 15413.6 | 22834.6 | 2599.1 | 9352.9 |
| | huFc-IL-7, q7d | AVG | 14.4 | 2559.0 | 28124.0 | 53573.6 | 59999.2 | 52932.8 | 41489.6 | 42899.2 |
| | | SEM | 6.5 | 408.9 | 2464.1 | 4911.5 | 6337.2 | 10998.2 | 4821.1 | 5013.0 |
| | human IL-7, q7d | AVG | 5.3 | 1550.7 | 4316.0 | 17802.7 | 28061.3 | 30177.3 | 24720.0 | 26104.0 |
| | | SEM | 3.5 | 403.5 | 542.7 | 3689.5 | 1484.5 | 2861.6 | 633.8 | 2085.3 |
| | human IL-7, q7d | AVG | 4.0 | 748.0 | 3179.0 | 19303.0 | 19203.0 | 17930.0 | 22460.0 | 21473.0 |
| | | SEM | 1.6 | 56.1 | 443.3 | 1666.1 | 1429.5 | 2511.6 | 4458.6 | 3199.5 |
| b.) B6.SJL Control mice | PBS | AVG | 15572.6 | | | | | | | |
| | | SEM | 1631.4 | | | | | | | |
| III. Donor Derived T-cells (CD45.1$^+$CD3$^+$abTCR$^+$) | | | | | | | | | | |
| a.) Allogeneic BMT into B6C3 mice | PBS | AVG | 0.0 | 206.7 | 192.0 | 1808.0 | 3928.0 | 4453.3 | 6178.7 | 5622.7 |
| | | SEM | 0.0 | 121.6 | 46.2 | 245.0 | 546.7 | 533.0 | 538.1 | 210.0 |
| | huFc-IL-7, q2d | AVG | 0.0 | 124.0 | 839.0 | 5260.8 | 12252.8 | 15204.8 | 16628.0 | 13365.6 |
| | | SEM | 0.0 | 24.9 | 155.5 | 1183.1 | 1734.8 | 1641.2 | 1524.5 | 1423.9 |
| | huFc-IL-7, q7d | AVG | 0.0 | 38.4 | 228.0 | 2428.0 | 5492.0 | 9988.0 | 9252.8 | 8598.4 |
| | | SEM | 0.0 | 6.1 | 38.5 | 326.2 | 918.1 | 2475.8 | 2748.6 | 1185.9 |
| | human IL-7, q7d | AVG | 0.0 | 56.0 | 144.0 | 1057.3 | 3068.0 | 5368.0 | 5081.3 | 7112.0 |
| | | SEM | 0.0 | 3.3 | 42.5 | 160.1 | 154.0 | 645.5 | 113.7 | 409.9 |
| | human IL-7, q7d | AVG | 0.0 | 41.0 | 88.0 | 1493.0 | 2579.0 | 3918.0 | 5021.0 | 6043.0 |
| | | SEM | 0.0 | 2.5 | 20.2 | 187.5 | 238.0 | 694.6 | 724.2 | 1013.1 |
| b.) B6.SJL Control mice | PBS | AVG | 10832.0 | | | | | | | |
| | | SEM | 1500.4 | | | | | | | |

EXAMPLE 9

Efficacy of huFc-IL-7 on T-Cell Transplantations in Lymphopenic Mice

The efficacy of huFc-IL-7 fusion proteins was also evaluated in a T-cell transplantation model. In essence, a homogeneous (clonal) population of T-cells was transferred into immunodeficient, irradiated mice, the recipient mice were administered the huFc-IL-7 fusion protein, and the degree of T-cell reconstitution and, eventually, T-cell function, was assessed.

To obtain a homogeneous population of T-cells, splenocytes were taken from P14 TCR-tg/RAG mice (Charles River Laboratories, Wilmington, Mass.), which are devoid of B-cells. In addition, all T-cells of these mice express the transgenic T-cell receptor (TCR), P14, which is specific for a viral epitope (gp33 of LCMV).

Single cell suspensions of splenocytes were injected intravenously into the tails of RAG $C\gamma^{-/-}$ immunodeficient mice (Charles River Laboratories) that had been irradiated once with 650 Rads (sub-lethal dose) 4 hrs prior to transplantation. On alternate days starting at Day 2, recipient mice were administered 7 μg of the fusion protein huFcγ2(h)(FN>AQ)-IL-7. A control group of recipient mice were administered PBS. The degree of T-cell reconstitution in response to the huFc-IL-7 fusion protein or PBS was determined by measuring the presence of P14 T-cells ($CD8^+V\beta8.1^+V\alpha2^+$ cells) in the blood by flow cytometry.

It was found that at Day 35, mice that were administered the huFc-IL-7 fusion protein had a 17-fold increase in T-cell numbers (35,000 cells/μl) compared to control mice (2,000 cells/μl). Indeed, the levels of T-cell reconstitution exceeded those seen in untreated P14 TCR mice (23,000 cells/μl). In addition, in these huFc-IL-7-treated mice a significant fraction of reconstituted T-cells had up-regulated the IL-2Rα receptor subunit, CD25, on the cell surface. Thus, not only was the huFc-IL-7 fusion protein useful in expanding transplanted T-cells, but in addition may have preconditioned the transferred T-cells to be responsive to cytokines, such as IL-2.

EXAMPLE 10 huFc-IL-7 Adjuvant Therapy for Immunocommomised Patients

Numerous clinical settings are envisaged in which patients may benefit from huFc-IL-7 adjuvant therapy. For example, new treatment modalities are being developed for pediatric patients with malignant disease such as lymphoblastic or myeloid leukemias, who, following a myeloablative therapy, are treated by allogeneic hematopoietic stem cell transplantation to reconstitute the immune system.

To increase markedly the potential donor pool for these patients, it has been found that G-CSF mobilized peripheral blood stem cells (PBSCs) from matched unrelated donors or haplo-identical donors with 1-3 HLA loci mismatches may be a source of cells, provided that the transplant is depleted of T-cells (see Handgretinger et al. (2001) *Annals NY Acad. Sciences* 938:340-357). This depletion drastically reduced the occurrence of acute graft-to-host transplant rejection (GvHD); however, it is believed that because of the low concentration of T-cells, there was a significant delay in immunoreconstitution. Patients were at high risk of viral infections for at least the first 6 month post transplant, and T-cells did not return to normal levels for a year (Handgretinger et al, (2001) *Annals NY Acad. Sciences* 938:340-357; Lang et al., (2003) *Blood* 101:1630-6). Therefore, it would be advantageous to increase the rate of repopulation of T-cells and of other immune cells in these patients.

Patients that will benefit huFc-IL-7 therapy include patients with a childhood leukemia, such as a lymphoblastic leukemia or a myeloid leukemia. Children having this disorder will first undergo a myeloablative conditioning therapy which may be based either on the chemotherapeutic agent busulfan or total body irradiation combined with chemotherapy. For instance, according to the patient's diagnosis and age, the patient is treated with total body irradiation (typically 6 treatments of 2 Gy each), rabbit antithymocyte globulin (10 mg/kg daily for 3 days), etoposide (40 mg/kg) and cyclophosphamide (120 mg/kg).

To obtain, CD34 positive (pos) stem cells for transplant, peripheral blood stem cells (PBSCs) of a histocompatible (allogeneic) donor are mobilized with a daily dose of 10 micrograms/kg of G-CSF for 6 days, and are harvested by leukapharesis on days 5 and 6. Generally, about $20\times10^6$/kg CD34 pos stem cells are obtained and transplanted. CD34 pos stem cells are purified from the PBSCs by positive selection with an antiCD34 antibody in a SuperMACS system (Magnetic activated cell sorting, Miltenyi Biotec) and eluted. T-cell depletion is typically around 5 logs, to about $10\times10^3$ cells/kg. Aggregates and other debris are excluded from the graft by FACS sorting. The cell suspension is infused into the patient via a central venous catheter. Optionally, the graft may include purified populations of other immune cells, such as haploidentical NK cells, DCs, monocytes, as well as CD34 neg stem cells.

To assess engraftment, an absolute neutrophil count is performed. Engraftment is considered successful once neutrophil levels remain above 50 cells/microliter. Reconstitution of immune cells is monitored by FACS analysis, weekly at first and, once T-cell recovery begins, every 3 months.

To augment immunoreconstitution, the patient is treated with a huFc-IL-7 fusion protein such as huFcγ2h(FN>AQ)-IL-7 or huFcγ1(YN>AQ)(linker2)-IL-7. Approximately 3 weeks after transplant (or after engraftment is established), the patient receives a subcutaneous administration of huFcγ2h(FN>AQ)-IL-7 or huFcγ1(YN>AQ)(linker2)-IL-7 at a dose of about 1.5 mg/$m^2$ (or a dose in the range of 0.15 mg/$m^2$ to 15 mg/$m^2$), about 2 times a week for 6 months-12 months, until T-cell counts reach 50% of normal levels. It is found that the prognosis of the patient is improved due to lowered risk of viral infection, one of the main post-transplant complications. It is further found that this treatment does not significantly increase the risk of acute GvHD.

In addition to administration of huFc-IL-7 protein, other medications are optimally given prophylactically. These include, for example, acyclovir, metronidazole, flucanazole and co-trimoxazole. For the first three months, the patient may receive weekly administration of immunoglobulins, as well as of G-CSF.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A fusion protein comprising:

a first portion comprising an Fc region from IgG1 or IgG2 wherein the Fc region comprises a hinge region, a CH2 domain, and a CH3 domain; and a second portion comprising a polypeptide having an amino acid sequence comprising at least 95% sequence identity with wild-type mature human interleukin-7 (IL-7) wherein wild-type mature human IL-7 consists of amino acid residues 26-176 of SEQ ID NO:1, and wherein amino acid residues corresponding to positions 70 and 91 of wild-type mature human IL-7 are glycosylated and the amino acid residue corresponding to position 116 of wild-type mature human IL-7 is non-glycosylated.

2. The fusion protein of claim 1, wherein the amino acid residue corresponding to position 116 of wild-type mature human IL-7 is asparagine.

3. The fusion protein of claim 1, wherein the polypeptide having 95% sequence identity with wild-type mature human IL-7 comprises disulfide bonding between residues corresponding to positions Cys2 and Cys92, Cys34 and Cys 129, and Cys47 and Cys 141 of wild-type mature human IL-7.

4. The fusion protein of claim 1, further comprising a linker between the first portion and the second portion.

5. The fusion protein of claim 1, wherein the Fc region is from IgG1.

6. The fusion protein of claim 5, wherein the Fc region further comprises an amino acid substituted in place of Asn297at glycosylation site of the Fc region.

7. The fusion protein of claim 6, wherein the Fc region further comprising an amino acid substituted in place of Tyr296 at the glycosylation site of the Fc region.

8. The fusion protein of claim 7, wherein Ala is substituted in place of Tyr296 and Gln is substituted in place of Asn297 at the glycosylation site of the Fc region.

9. The fusion protein of claim 1, wherein the Fc region is from IgG2.

10. The fusion protein of claim 9, wherein the Fc region further comprises an IgG1 hinge.

11. The fusion protein of claim 9, wherein the Fc region further comprises an amino acid substituted in place of Asn at glycosylation site of the Fc region.

12. The fusion protein of claim 11, wherein the Fc region further comprises an amino acid substituted in place of the Phe residue adjacent the Asn residue at the glycosylation site of the Fc region.

13. The fusion protein of claim 12, wherein Ala is substituted in place of Phe and Gln is substituted in place of Asn at the glycosylation site of the Fc region.

14. The fusion protein of claim 1, wherein said second portion comprises wild-type mature human IL-7 consisting of amino acid residues 26-176 of SEQ ID NO:1, and wherein the amino acid residues corresponding to positions 70 and 91 of said wild-type mature human IL-7 are glycosylated and the amino acid residue corresponding to position 116 of said wild-type mature human IL-7 is non-glycosylated.

15. A purified nucleic acid encoding the fusion protein of claim 1.

16. A cultured host cell comprising the nucleic acid of claim 15.

17. A fusion protein comprising:

a first portion comprising an Fc region from IgG1 or IgG2 wherein the Fc region comprises a hinge region, a CH2 domain, and a CH3 domain;

and a second portion comprising an amino acid sequence that is at least 95% identical to amino acid residues 26-176 of SEQ ID NO:1 (wild-type mature human IL-7) except that residues 121 to 138 of SEQ ID NO:1 are deleted in said second portion, and wherein the amino acid residues corresponding to positions 70 and 91 of wild-type mature human IL-7 are glycosylated and the amino acid residue corresponding to position 116 of wild-type mature human IL-7 is non-glycosylated.

* * * * *

SEQUENCE LISTING

```
<160> NUMBER OF SEQ ID NOS: 38

<210> SEQ ID NO 1
<211> LENGTH: 177
<212> TYPE: PRT
<213> ORGANISM: Homo sapiens

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30
```

-continued

```
Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His


<210> SEQ ID NO 2
<211> LENGTH: 176
<212> TYPE: PRT
<213> ORGANISM: Bos taurus

<400> SEQUENCE: 2

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Ile Ser Gly Arg
            20                  25                  30

Asp Gly Gly Ala Tyr Gln Asn Val Leu Met Val Asn Ile Asp Asp Leu
        35                  40                  45

Asp Asn Met Ile Asn Phe Asp Ser Asn Cys Leu Asn Asn Glu Pro Asn
    50                  55                  60

Phe Phe Lys Lys His Ser Cys Asp Asp Asn Lys Glu Ala Ser Phe Leu
65                  70                  75                  80

Asn Arg Ala Ser Arg Lys Leu Arg Gln Phe Leu Lys Met Asn Ile Ser
                85                  90                  95

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
        115                 120                 125

Ser Glu Ala Gln Pro Thr Lys Asn Leu Glu Glu Asn Lys Ser Ser Arg
    130                 135                 140

Glu Gln Lys Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Lys Glu His
                165                 170                 175


<210> SEQ ID NO 3
<211> LENGTH: 176
<212> TYPE: PRT
<213> ORGANISM: Ovis aries

<400> SEQUENCE: 3

Met Phe His Val Ser Phe Arg Tyr Ile Phe Gly Ile Pro Pro Leu Ile
```

-continued

```
1               5                   10                  15

Leu Val Leu Leu Pro Val Ala Ser Ser Asp Cys Asp Phe Ser Gly Lys
            20                  25                  30

Asp Gly Gly Ala Tyr Gln Asn Val Leu Met Val Ser Ile Asp Asp Leu
        35                  40                  45

Asp Asn Met Ile Asn Phe Asp Ser Asn Cys Leu Asn Asn Glu Pro Asn
    50                  55                  60

Phe Phe Lys Lys His Ser Cys Asp Asp Asn Lys Glu Ala Ser Phe Leu
65                  70                  75                  80

Asn Arg Ala Ala Arg Lys Leu Lys Gln Phe Leu Lys Met Asn Ile Ser
                85                  90                  95

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
        115                 120                 125

Gly Glu Ala Gln Pro Thr Lys Asn Leu Glu Glu Asn Lys Ser Leu Lys
    130                 135                 140

Glu Gln Arg Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Thr Glu His
                165                 170                 175


<210> SEQ ID NO 4
<211> LENGTH: 384
<212> TYPE: PRT
<213> ORGANISM: Artificial Sequence
<220> FEATURE:
<223> OTHER INFORMATION: Human Fc-gamma1-IL-7

<400> SEQUENCE: 4

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
```

-continued

```
        195                 200                 205

Ser Cys Ser Val Met His Glu Ala Leu His Asn His Tyr Thr Gln Lys
    210                 215                 220

Ser Ala Thr Ala Thr Pro Gly Ala Asp Cys Asp Ile Glu Gly Lys Asp
225                 230                 235                 240

Gly Lys Gln Tyr Glu Ser Val Leu Met Val Ser Ile Asp Gln Leu Leu
                245                 250                 255

Asp Ser Met Lys Glu Ile Gly Ser Asn Cys Leu Asn Asn Glu Phe Asn
            260                 265                 270

Phe Phe Lys Arg His Ile Cys Asp Ala Asn Lys Glu Gly Met Phe Leu
        275                 280                 285

Phe Arg Ala Ala Arg Lys Leu Arg Gln Phe Leu Lys Met Asn Ser Thr
    290                 295                 300

Gly Asp Phe Asp Leu His Leu Leu Lys Val Ser Glu Gly Thr Thr Ile
305                 310                 315                 320

Leu Leu Asn Cys Thr Gly Gln Val Lys Gly Arg Lys Pro Ala Ala Leu
                325                 330                 335

Gly Glu Ala Gln Pro Thr Lys Ser Leu Glu Glu Asn Lys Ser Leu Lys
            340                 345                 350

Glu Gln Lys Lys Leu Asn Asp Leu Cys Phe Leu Lys Arg Leu Leu Gln
        355                 360                 365

Glu Ile Lys Thr Cys Trp Asn Lys Ile Leu Met Gly Thr Lys Glu His
    370                 375                 380


<210> SEQ ID NO 5
<211> LENGTH: 383
<212> TYPE: PRT
<213> ORGANISM: Artificial Sequence
<220> FEATURE:
<223> OTHER INFORMATION: Human Fc-gamma2(h)(FN>AQ)-IL-7

<400> SEQUENCE: 5

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Ala
65                  70                  75                  80

Gln Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
```

-continued

```
        180                 185                 190

Lys Leu Thr Val Asp Lys Ser Arg Trp Gln Gln Gly Asn Val Phe Ser
    195                 200                 205

Cys Ser Val Met His Glu Ala Leu His Asn His Tyr Thr Gln Lys Ser
    210                 215                 220

Ala Thr Ala Thr Pro Gly Ala Asp Cys Asp Ile Glu Gly Lys Asp Gly
225                 230                 235                 240

Lys Gln Tyr Glu Ser Val Leu Met Val Ser Ile Asp Gln Leu Leu Asp
                245                 250                 255

Ser Met Lys Glu Ile Gly Ser Asn Cys Leu Asn Asn Glu Phe Asn Phe
            260                 265                 270

Phe Lys Arg His Ile Cys Asp Ala Asn Lys Glu Gly Met Phe Leu Phe
        275                 280                 285

Arg Ala Ala Arg Lys Leu Arg Gln Phe Leu Lys Met Asn Ser Thr Gly
    290                 295                 300

Asp Phe Asp Leu His Leu Leu Lys Val Ser Glu Gly Thr Thr Ile Leu
305                 310                 315                 320

Leu Asn Cys Thr Gly Gln Val Lys Gly Arg Lys Pro Ala Ala Leu Gly
                325                 330                 335

Glu Ala Gln Pro Thr Lys Ser Leu Glu Glu Asn Lys Ser Leu Lys Glu
            340                 345                 350

Gln Lys Lys Leu Asn Asp Leu Cys Phe Leu Lys Arg Leu Leu Gln Glu
        355                 360                 365

Ile Lys Thr Cys Trp Asn Lys Ile Leu Met Gly Thr Lys Glu His
    370                 375                 380
```

<210> SEQ ID NO 6
<211> LENGTH: 398
<212> TYPE: PRT
<213> ORGANISM: Artificial Sequence
<220> FEATURE:
<223> OTHER INFORMATION: Human FC-gamma1(linker1)-IL-7

<400> SEQUENCE: 6

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

-continued

```
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Ala Thr Ala Thr Pro Gly Ala Gly Gly Gly Gly Ser Gly Gly Gly
225                 230                 235                 240

Gly Ser Gly Gly Gly Ser Asp Cys Asp Ile Glu Gly Lys Asp Gly Lys
                245                 250                 255

Gln Tyr Glu Ser Val Leu Met Val Ser Ile Asp Gln Leu Leu Asp Ser
            260                 265                 270

Met Lys Glu Ile Gly Ser Asn Cys Leu Asn Asn Glu Phe Asn Phe Phe
        275                 280                 285

Lys Arg His Ile Cys Asp Ala Asn Lys Glu Gly Met Phe Leu Phe Arg
    290                 295                 300

Ala Ala Arg Lys Leu Arg Gln Phe Leu Lys Met Asn Ser Thr Gly Asp
305                 310                 315                 320

Phe Asp Leu His Leu Leu Lys Val Ser Glu Gly Thr Thr Ile Leu Leu
                325                 330                 335

Asn Cys Thr Gly Gln Val Lys Gly Arg Lys Pro Ala Ala Leu Gly Glu
            340                 345                 350

Ala Gln Pro Thr Lys Ser Leu Glu Glu Asn Lys Ser Leu Lys Glu Gln
        355                 360                 365

Lys Lys Leu Asn Asp Leu Cys Phe Leu Lys Arg Leu Leu Gln Glu Ile
    370                 375                 380

Lys Thr Cys Trp Asn Lys Ile Leu Met Gly Thr Lys Glu His
385                 390                 395


<210> SEQ ID NO 7
<211> LENGTH: 393
<212> TYPE: PRT
<213> ORGANISM: Artificial Sequence
<220> FEATURE:
<223> OTHER INFORMATION: Human Fc-gamma1(YN>AQ)(linker2)-IL-7

<400> SEQUENCE: 7

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Ala Gln Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
```

-continued

```
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Ala Thr Ala Thr Pro Gly Ala Gly Gly Gly Gly Ser Gly Gly Gly
225                 230                 235                 240

Gly Asp Cys Asp Ile Glu Gly Lys Asp Gly Lys Gln Tyr Glu Ser Val
                245                 250                 255

Leu Met Val Ser Ile Asp Gln Leu Leu Asp Ser Met Lys Glu Ile Gly
            260                 265                 270

Ser Asn Cys Leu Asn Asn Glu Phe Asn Phe Phe Lys Arg His Ile Cys
        275                 280                 285

Asp Ala Asn Lys Glu Gly Met Phe Leu Phe Arg Ala Ala Arg Lys Leu
    290                 295                 300

Arg Gln Phe Leu Lys Met Asn Ser Thr Gly Asp Phe Asp Leu His Leu
305                 310                 315                 320

Leu Lys Val Ser Glu Gly Thr Thr Ile Leu Leu Asn Cys Thr Gly Gln
                325                 330                 335

Val Lys Gly Arg Lys Pro Ala Ala Leu Gly Glu Ala Gln Pro Thr Lys
            340                 345                 350

Ser Leu Glu Glu Asn Lys Ser Leu Lys Glu Gln Lys Lys Leu Asn Asp
        355                 360                 365

Leu Cys Phe Leu Lys Arg Leu Leu Gln Glu Ile Lys Thr Cys Trp Asn
    370                 375                 380

Lys Ile Leu Met Gly Thr Lys Glu His
385                 390


<210> SEQ ID NO 8
<211> LENGTH: 391
<212> TYPE: PRT
<213> ORGANISM: Artificial Sequence
<220> FEATURE:
<223> OTHER INFORMATION: Human Fc-gamma1(YN>AQ,d)(linker2)-IL-7

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Ala Gln Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
```

-continued

```
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Ala Thr Ala Thr Pro Gly Gly Gly Gly Ser Gly Gly Gly Gly Asp
225                 230                 235                 240

Cys Asp Ile Glu Gly Lys Asp Gly Lys Gln Tyr Glu Ser Val Leu Met
                245                 250                 255

Val Ser Ile Asp Gln Leu Leu Asp Ser Met Lys Glu Ile Gly Ser Asn
            260                 265                 270

Cys Leu Asn Asn Glu Phe Asn Phe Phe Lys Arg His Ile Cys Asp Ala
        275                 280                 285

Asn Lys Glu Gly Met Phe Leu Phe Arg Ala Ala Arg Lys Leu Arg Gln
    290                 295                 300

Phe Leu Lys Met Asn Ser Thr Gly Asp Phe Asp Leu His Leu Leu Lys
305                 310                 315                 320

Val Ser Glu Gly Thr Thr Ile Leu Leu Asn Cys Thr Gly Gln Val Lys
                325                 330                 335

Gly Arg Lys Pro Ala Ala Leu Gly Glu Ala Gln Pro Thr Lys Ser Leu
            340                 345                 350

Glu Glu Asn Lys Ser Leu Lys Glu Gln Lys Lys Leu Asn Asp Leu Cys
        355                 360                 365

Phe Leu Lys Arg Leu Leu Gln Glu Ile Lys Thr Cys Trp Asn Lys Ile
    370                 375                 380

Leu Met Gly Thr Lys Glu His
385                 390


<210> SEQ ID NO 9
<211> LENGTH: 18
<212> TYPE: PRT
<213> ORGANISM: Artificial Sequence
<220> FEATURE:
<223> OTHER INFORMATION: Eighteen amino acid internal deletion in the
      IL-7 moiety

<400> SEQUENCE: 9

Val Lys Gly Arg Lys Pro Ala Ala Leu Gly Glu Ala Gln Pro Thr Lys
1               5                   10                  15

Ser Leu


<210> SEQ ID NO 10
<211> LENGTH: 5
<212> TYPE: PRT
<213> ORGANISM: Artificial Sequence
<220> FEATURE:
<223> OTHER INFORMATION: End of Fc portion of huFc-gamma1
```

-continued (YN>AQ,d)(linker2)-IL-7

<400> SEQUENCE: 10

Ala Thr Ala Thr Pro
1 5

<210> SEQ ID NO 11
<211> LENGTH: 7
<212> TYPE: PRT
<213> ORGANISM: Artificial Sequence
<220> FEATURE:
<223> OTHER INFORMATION: End of Fc portion of huFc-gamma1 (YN>AQ)(linker2)-IL-7

<400> SEQUENCE: 11

Ala Thr Ala Thr Pro Gly Ala
1 5

<210> SEQ ID NO 12
<211> LENGTH: 20
<212> TYPE: DNA
<213> ORGANISM: Artificial Sequence
<220> FEATURE:
<223> OTHER INFORMATION: Primer 2 for huFc-gamma1(YN>AQ,d)(linker2)-IL-7

<400> SEQUENCE: 12
atcatgtctg gatccctcga 20

<210> SEQ ID NO 13
<211> LENGTH: 13
<212> TYPE: PRT
<213> ORGANISM: Homo sapiens

<400> SEQUENCE: 13

Pro Thr Lys Ser Leu Glu Glu Asn Lys Ser Leu Lys Glu
1 5 10

<210> SEQ ID NO 14
<211> LENGTH: 20
<212> TYPE: DNA
<213> ORGANISM: Artificial Sequence
<220> FEATURE:
<223> OTHER INFORMATION: Primer 2 for huFc-gamma1(YN>AQ)(linker2)-IL-7

<400> SEQUENCE: 14
atcatgtctg gatccctcga 20

<210> SEQ ID NO 15
<211> LENGTH: 62
<212> TYPE: DNA
<213> ORGANISM: Artificial Sequence
<220> FEATURE:
<223> OTHER INFORMATION: Primer 1 for huFc-gamma1(YN>AQ)(linker2)-IL-7

<400> SEQUENCE: 15
cccgggcgcc ggcggtggag gatcaggtgg tggcggtgat tgtgatattg aaggtaaaga 60
tg 62

<210> SEQ ID NO 16
<211> LENGTH: 56
<212> TYPE: DNA
<213> ORGANISM: Artificial Sequence
<220> FEATURE:
<223> OTHER INFORMATION: Primer 1 for huFc-gamma1(YN>AQ,d)(linker2)-IL-7

<400> SEQUENCE: 16

-continued

```
cccgggcggt ggaggatcag gtggtggcgg tgattgtgat attgaaggta aagatg        56


<210> SEQ ID NO 17
<211> LENGTH: 7
<212> TYPE: DNA
<213> ORGANISM: Artificial Sequence
<220> FEATURE:
<223> OTHER INFORMATION: SmaI site on a primer

<400> SEQUENCE: 17

cccgggt                                                               7


<210> SEQ ID NO 18
<211> LENGTH: 48
<212> TYPE: DNA
<213> ORGANISM: Artificial Sequence
<220> FEATURE:
<223> OTHER INFORMATION: Synthetic oligonuclotide duplex for generation
      of huFc-gamma1(linker1)-IL-7

<400> SEQUENCE: 18

gggtgcaggg ggcgggggca gcgggggcgg aggatccggc gggggctc                 48


<210> SEQ ID NO 19
<211> LENGTH: 908
<212> TYPE: DNA
<213> ORGANISM: Artificial Sequence
<220> FEATURE:
<223> OTHER INFORMATION: Nucleic acid sequence for the Fc region of
      human Fc-gamma2(h)(FN>AQ)

<400> SEQUENCE: 19

gagcccaaat cttctgacaa aactcacaca tgcccaccgt gcccaggtaa gccagcccag     60

gcctcgccct ccagctcaag gcgggacagg tgccctagag tagcctgcat ccagggacag    120

gccccagctg ggtgctgaca cgtccacctc catctcttcc tcagcaccac ctgtggcagg    180

accgtcagtc ttcctcttcc ccccaaaacc caaggacacc ctcatgatct cccggacccc    240

tgaggtcacg tgcgtggtgg tggacgtgag ccacgaagac cccgaggtcc agttcaactg    300

gtacgtggac ggcgtggagg tgcataatgc caagacaaag ccacgggagg agcaggccca    360

gagcacgttc cgtgtggtca gcgtcctcac cgttgtgcac caggactggc tgaacggcaa    420

ggagtacaag tgcaaggtct ccaacaaagg cctcccagcc cccatcgaga aaaccatctc    480

caaaaccaaa ggtgggaccc gcggggtatg agggccacat ggacagaggc cggctcggcc    540

caccctctgc cctgagagtg accgctgtac caacctctgt ccctacaggg cagccccgag    600

aaccacaggt gtacaccctg cccccatcac gggaggagat gaccaagaac caggtcagcc    660

tgacctgcct ggtcaaaggc ttctacccca gcgacatcgc cgtggagtgg gagagcaatg    720

ggcagccgga gaacaactac aagaccacac ctcccatgct ggactccgac ggctccttct    780

tcctctacag caagctcacc gtggacaaga gcaggtggca gcaggggaac gtcttctcat    840

gctccgtgat gcatgaggct ctgcacaacc actacacaca gaagagcgcc accgcgaccc    900

cgggtgca                                                             908


<210> SEQ ID NO 20
<211> LENGTH: 908
<212> TYPE: DNA
<213> ORGANISM: Artificial Sequence
<220> FEATURE:
<223> OTHER INFORMATION: Nucleic acid sequence for the Fc region of
      human Fc-gamma2(h)
```

-continued

<400> SEQUENCE: 20
gagcccaaat cttctgacaa aactcacaca tgcccaccgt gcccaggtaa gccagcccag 60
gcctcgccct ccagctcaag gcgggacagg tgccctagag tagcctgcat ccagggacag 120
gccccagctg ggtgctgaca cgtccacctc catctcttcc tcagcaccac ctgtggcagg 180
accgtcagtc ttcctcttcc ccccaaaacc caaggacacc ctcatgatct cccggacccc 240
tgaggtcacg tgcgtggtgg tggacgtgag ccacgaagac cccgaggtcc agttcaactg 300
gtacgtggac ggcgtggagg tgcataatgc caagacaaag ccacgggagg agcagttcaa 360
cagcacgttc cgtgtggtca gcgtcctcac cgttgtgcac caggactggc tgaacggcaa 420
ggagtacaag tgcaaggtct ccaacaaagg cctcccagcc cccatcgaga aaaccatctc 480
caaaaccaaa ggtgggaccc gcggggtatg agggccacat ggacagaggc cggctcggcc 540
caccctctgc cctgagagtg accgctgtac caacctctgt ccctacaggg cagccccgag 600
aaccacaggt gtacaccctg cccccatcac gggaggagat gaccaagaac caggtcagcc 660
tgacctgcct ggtcaaaggc ttctacccca gcgacatcgc cgtggagtgg gagagcaatg 720
ggcagccgga gaacaactac aagaccacac ctcccatgct ggactccgac ggctccttct 780
tcctctacag caagctcacc gtggacaaga gcaggtggca gcaggggaac gtcttctcat 840
gctccgtgat gcatgaggct ctgcacaacc actacacaca gaagagcgcc accgcgaccc 900
cgggcgcc 908

<210> SEQ ID NO 21
<211> LENGTH: 911
<212> TYPE: DNA
<213> ORGANISM: Artificial Sequence
<220> FEATURE:
<223> OTHER INFORMATION: Nucleic acid sequence for the Fc region of human Fc-gamma1 (YN>AQ)

<400> SEQUENCE: 21
gagcccaaat cttctgacaa aactcacaca tgcccaccgt gcccaggtaa gccagcccag 60
gcctcgccct ccagctcaag gcgggacagg tgccctagag tagcctgcat ccagggacag 120
gccccagccg ggtgctgaca cgtccacctc catctcttcc tcagcacctg aactcctggg 180
gggaccgtca gtcttcctct tccccccaaa acccaaggac accctcatga tctcccggac 240
ccctgaggtc acatgcgtgg tggtggacgt gagccacgaa gaccctgagg tcaagttcaa 300
ctggtacgtg gacggcgtgg aggtgcataa tgccaagaca aagccgcggg aggagcaggc 360
ccagagcacg taccgtgtgg tcagcgtcct caccgtcctg caccaggact ggctgaatgg 420
caaggagtac aagtgcaagg tctccaacaa agccctccca gcccccatcg agaaaaccat 480
ctccaaagcc aaaggtggga cccgtggggt gcgagggcca catggacaga ggccggctcg 540
gcccaccctc tgccctgaga gtgaccgctg taccaacctc tgtccctaca gggcagcccc 600
gagaaccaca ggtgtacacc ctgcccccat cacgggagga gatgaccaag aaccaggtca 660
gcctgacctg cctggtcaaa ggcttctatc ccagcgacat cgccgtggag tgggagagca 720
atgggcagcc ggagaacaac tacaagacca cgcctcccgt gctggactcc gacggctcct 780
tcttcctcta tagcaagctc accgtggaca agagcaggtg gcagcagggg aacgtcttct 840
catgctccgt gatgcatgag gctctgcaca accactacac gcagaagagc gccaccgcga 900
ccccgggcgc c 911

-continued

<210> SEQ ID NO 22
<211> LENGTH: 911
<212> TYPE: DNA
<213> ORGANISM: Artificial Sequence
<220> FEATURE:
<223> OTHER INFORMATION: Nucleic acid for the Fc region of human
Fc-gamma1

<400> SEQUENCE: 22
gagcccaaat cttctgacaa aactcacaca tgcccaccgt gcccaggtaa gccagcccag 60
gcctcgccct ccagctcaag gcgggacagg tgccctagag tagcctgcat ccagggacag 120
gccccagccg ggtgctgaca cgtccacctc catctcttcc tcagcacctg aactcctggg 180
gggaccgtca gtcttcctct tcccccaaa acccaaggac accctcatga tctcccggac 240
ccctgaggtc acatgcgtgg tggtggacgt gagccacgaa gaccctgagg tcaagttcaa 300
ctggtacgtg gacggcgtgg aggtgcataa tgccaagaca aagccgcggg aggagcagta 360
caacagcacg taccgtgtgg tcagcgtcct caccgtcctg caccaggact ggctgaatgg 420
caaggagtac aagtgcaagg tctccaacaa agccctccca gcccccatcg agaaaaccat 480
ctccaaagcc aaaggtggga cccgtggggt gcgagggcca catggacaga ggccggctcg 540
gcccaccctc tgccctgaga gtgaccgctg taccaacctc tgtccctaca gggcagcccc 600
gagaaccaca ggtgtacacc ctgcccccat cacgggagga gatgaccaag aaccaggtca 660
gcctgacctg cctggtcaaa ggcttctatc ccagcgacat cgccgtggag tgggagagca 720
atgggcagcc ggagaacaac tacaagacca cgcctcccgt gctggactcc gacggctcct 780
tcttcctcta tagcaagctc accgtggaca agagcaggtg gcagcagggg aacgtcttct 840
catgctccgt gatgcatgag gctctgcaca accactacac gcagaagagc gccaccgcga 900
ccccgggcgc c 911

<210> SEQ ID NO 23
<211> LENGTH: 9
<212> TYPE: DNA
<213> ORGANISM: Artificial Sequence
<220> FEATURE:
<223> OTHER INFORMATION: Beginning of the hinge region as shown in
Figure 20

<400> SEQUENCE: 23 gagcccaaa 9

<210> SEQ ID NO 24
<211> LENGTH: 7
<212> TYPE: DNA
<213> ORGANISM: Artificial Sequence
<220> FEATURE:
<223> OTHER INFORMATION: AflII sequence

<400> SEQUENCE: 24 cttaagc 7

<210> SEQ ID NO 25
<211> LENGTH: 9
<212> TYPE: PRT
<213> ORGANISM: Artificial Sequence
<220> FEATURE:
<223> OTHER INFORMATION: Linker 2 for Fc-IL-7 fusion proteins

<400> SEQUENCE: 25

Gly Gly Gly Gly Ser Gly Gly Gly Gly
1 5

-continued

<210> SEQ ID NO 26
<211> LENGTH: 4
<212> TYPE: PRT
<213> ORGANISM: Artificial Sequence
<220> FEATURE:
<223> OTHER INFORMATION: Replacement sequence near the C-terminus of the Fc portion of an immunoglobulin heavy chain

<400> SEQUENCE: 26

Ala Thr Ala Thr
1

<210> SEQ ID NO 27
<211> LENGTH: 4
<212> TYPE: PRT
<213> ORGANISM: Artificial Sequence
<220> FEATURE:
<223> OTHER INFORMATION: Sequence near the C-terminus of the Fc portion of an immunoglobulin heavy chain

<400> SEQUENCE: 27

Leu Ser Leu Ser
1

<210> SEQ ID NO 28
<211> LENGTH: 4
<212> TYPE: PRT
<213> ORGANISM: Artificial Sequence
<220> FEATURE:
<223> OTHER INFORMATION: Replacement sequence within an IgG1 heavy chain

<400> SEQUENCE: 28

Gln Ala Gln Ser
1

<210> SEQ ID NO 29
<211> LENGTH: 4
<212> TYPE: PRT
<213> ORGANISM: Artificial Sequence
<220> FEATURE:
<223> OTHER INFORMATION: Sequence within an IgG1 heavy chain

<400> SEQUENCE: 29

Gln Phe Asn Ser
1

<210> SEQ ID NO 30
<211> LENGTH: 4
<212> TYPE: PRT
<213> ORGANISM: Artificial Sequence
<220> FEATURE:
<223> OTHER INFORMATION: Sequence from IgG1

<400> SEQUENCE: 30

Gln Tyr Asn Ser
1

<210> SEQ ID NO 31
<211> LENGTH: 5
<212> TYPE: PRT
<213> ORGANISM: Artificial Sequence
<220> FEATURE:
<223> OTHER INFORMATION: Sequence from IL-7

<400> SEQUENCE: 31

Met Asn Ser Thr Gly

-continued

```
1               5


<210> SEQ ID NO 32
<211> LENGTH: 5
<212> TYPE: PRT
<213> ORGANISM: Artificial Sequence
<220> FEATURE:
<223> OTHER INFORMATION: Sequence from IL-7

<400> SEQUENCE: 32

Leu Asn Cys Thr Gly
1               5


<210> SEQ ID NO 33
<211> LENGTH: 21
<212> TYPE: DNA
<213> ORGANISM: Artificial Sequence
<220> FEATURE:
<223> OTHER INFORMATION: Flanking reverse primer for generation of
      Fc-gamma1-IL-7 fusion proteins

<400> SEQUENCE: 33

cagggtgtac acctgtggtt c                                              21


<210> SEQ ID NO 34
<211> LENGTH: 15
<212> TYPE: PRT
<213> ORGANISM: Artificial Sequence
<220> FEATURE:
<223> OTHER INFORMATION: Linker 1 for generation of Fc-IL-7 fusion
      proteins

<400> SEQUENCE: 34

Gly Gly Gly Gly Ser Gly Gly Gly Gly Ser Gly Gly Gly Gly Ser
1               5                   10                  15


<210> SEQ ID NO 35
<211> LENGTH: 6
<212> TYPE: PRT
<213> ORGANISM: Artificial Sequence
<220> FEATURE:
<223> OTHER INFORMATION: Sequence from IL-7

<400> SEQUENCE: 35

Ser Leu Glu Glu Asn Lys
1               5


<210> SEQ ID NO 36
<211> LENGTH: 28
<212> TYPE: DNA
<213> ORGANISM: Artificial Sequence
<220> FEATURE:
<223> OTHER INFORMATION: Mutagenic primer in the sense direction

<400> SEQUENCE: 36

agcaggccca gagcacgtac cgtgtggt                                       28


<210> SEQ ID NO 37
<211> LENGTH: 28
<212> TYPE: DNA
<213> ORGANISM: Artificial Sequence
<220> FEATURE:
<223> OTHER INFORMATION: Complementary strand of the mutagenic primer in
      the sense direction

<400> SEQUENCE: 37

gtacgtgctc tgggcctgct cctcccgc                                       28
```

-continued

```
<210> SEQ ID NO 38
<211> LENGTH: 21
<212> TYPE: DNA
<213> ORGANISM: Artificial Sequence
<220> FEATURE:
<223> OTHER INFORMATION: Flanking forward primer

<400> SEQUENCE: 38

ctctctgcag agcccaaatc t                                            21
```